US011484209B1

(12) United States Patent
Mao et al.

(10) Patent No.: US 11,484,209 B1
(45) Date of Patent: *Nov. 1, 2022

(54) METHOD OF MAKING A BONE OXYGENATION MEASUREMENT PROBE

(71) Applicant: ViOptix, Inc., Newark, CA (US)

(72) Inventors: Jimmy Jian-Min Mao, Fremont, CA (US); Robert E. Lash, Redwood City, CA (US)

(73) Assignee: ViOptix, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/165,847

(22) Filed: Feb. 2, 2021

Related U.S. Application Data

(60) Division of application No. 15/813,074, filed on Nov. 14, 2017, now Pat. No. 10,905,332, which is a continuation of application No. 14/446,222, filed on Jul. 29, 2014, now Pat. No. 9,814,393, which is a continuation of application No. 12/711,010, filed on Feb. 23, 2010, now Pat. No. 8,792,951.

(51) Int. Cl.
*H01S 4/00* (2006.01)
*A61B 5/00* (2006.01)
*A61B 5/1455* (2006.01)
*A61B 5/1459* (2006.01)

(52) U.S. Cl.
CPC .......... *A61B 5/0084* (2013.01); *A61B 5/1459* (2013.01); *A61B 5/14552* (2013.01); *A61B 5/4504* (2013.01); *A61B 5/6847* (2013.01); *A61B 5/7221* (2013.01); *A61B 5/725* (2013.01); *A61B 2562/0238* (2013.01); *Y10T 29/49002* (2015.01); *Y10T 29/49169* (2015.01)

(58) Field of Classification Search
CPC ............ A61B 5/14552; A61B 5/14542; A61B 5/4509; A61B 5/4504; A61B 5/0261; A61M 2039/082; Y10T 29/49169; Y10T 29/49002
USPC ........................ 29/592.1, 429, 593, 829, 854
See application file for complete search history.

(56) References Cited

U.S. PATENT DOCUMENTS

| | | | |
|---|---|---|---|
| 2,198,319 | A | 10/1938 | Silverman |
| 4,609,370 | A | 9/1986 | Morrison |
| 5,127,407 | A | 7/1992 | Tan |

(Continued)

OTHER PUBLICATIONS

R. Bonner et al., "Model for laser Doppler measurements of blood flow in tissue", Applied Optics, vol. 20, No. 12, 2097-2107 (1981).

(Continued)

*Primary Examiner* — Thiem D Phan
(74) *Attorney, Agent, or Firm* — Aka Chan LLP

(57) ABSTRACT

A bone oximeter probe includes an elongated member and a sensor head at an end of the elongated member to make measurements for a bone. The measurements can indicate the viability or nonviability of the bone. In an implementation, the probe is advanced through an incision in soft tissue, towards the underlying bone, and positioned so that the sensor head faces the bone to be measured. Optical signals are sent from the sensor head and into the bone. The bone reflects some of the optical signals which are then detected so that measurements for the bone can be made. Some of these measurements include an oxygen saturation level value, and a total hemoglobin concentration value of the bone.

15 Claims, 14 Drawing Sheets

(56) References Cited

U.S. PATENT DOCUMENTS

| | | |
|---|---|---|
| 5,183,464 A | 2/1993 | Dubrul et al. |
| 5,282,464 A | 2/1994 | Brain |
| 5,551,424 A | 9/1996 | Morrison et al. |
| 5,746,210 A | 5/1998 | Benaron et al. |
| 5,752,519 A | 5/1998 | Benaron et al. |
| 5,762,609 A | 6/1998 | Benaron et al. |
| 5,769,076 A | 6/1998 | Maekawa et al. |
| 5,842,982 A * | 12/1998 | Mannheimer ........ A61B 5/6829 600/340 |
| 5,879,294 A | 3/1999 | Anderson et al. |
| 6,246,901 B1 | 6/2001 | Benaron |
| 6,322,507 B1 | 11/2001 | Passi et al. |
| 6,498,942 B1 * | 12/2002 | Esenaliev ............ A61B 5/4076 600/323 |
| 6,517,530 B1 | 2/2003 | Kleven |
| 6,594,518 B1 | 7/2003 | Benaron et al. |
| 6,702,746 B1 | 3/2004 | Sronji |
| 7,108,696 B2 | 9/2006 | Daniel et al. |
| 7,207,949 B2 | 4/2007 | Miles et al. |
| 7,331,943 B2 | 2/2008 | Mascitelli et al. |
| 7,355,688 B2 | 4/2008 | Lash et al. |
| 7,488,292 B2 | 2/2009 | Adachi |
| 7,522,953 B2 | 4/2009 | Kaula et al. |
| 7,525,647 B2 | 4/2009 | Lash et al. |
| 7,538,865 B2 | 5/2009 | Lash et al. |
| 7,729,749 B2 | 6/2010 | Roessler et al. |
| 7,753,903 B1 | 7/2010 | Burton et al. |
| 10,178,968 B2 | 1/2019 | Mao et al. |
| 2005/0149035 A1 | 7/2005 | Pimenta et al. |
| 2008/0106792 A1 | 5/2008 | Lash et al. |
| 2008/0108886 A1 | 5/2008 | Lash et al. |
| 2008/0319290 A1 | 12/2008 | Mao et al. |

OTHER PUBLICATIONS

P. Elter et al., "Noninvasive, real time laser Doppler flowmetry in perfusion regions and larger vessels", SPIE proceesing. vol. 3570, 244-254 (1998).

* cited by examiner

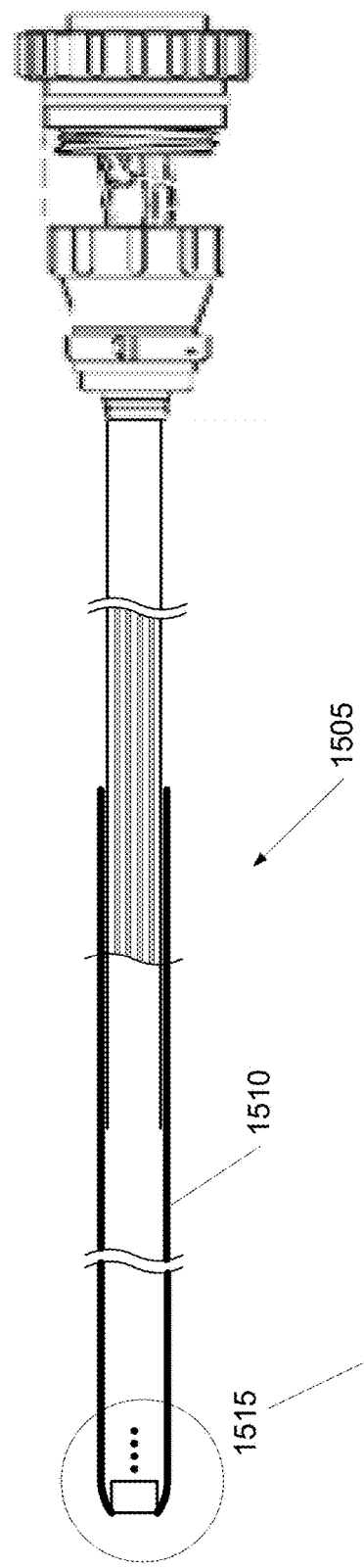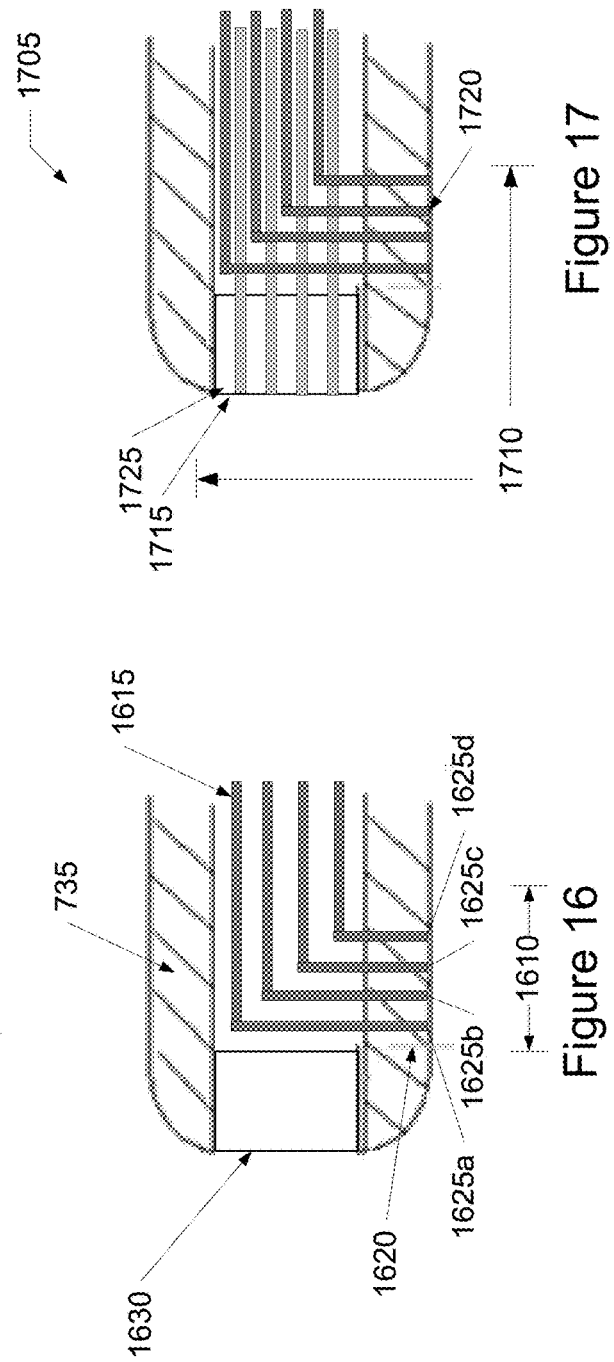

METHOD OF MAKING A BONE OXYGENATION MEASUREMENT PROBE

CROSS-REFERENCE TO RELATED APPLICATIONS

This patent application is a divisional of U.S. patent application Ser. No. 15/813,074, filed Nov. 14, 2017, issued as U.S. Pat. No. 10,905,332 on Feb. 2, 2021, which is continuation of U.S. patent application Ser. No. 14/446,222, filed Jul. 29, 2017, issued as U.S. Pat. No. 9,814,393 on Nov. 14, 2017, which is a continuation of U.S. patent application Ser. No. 12/711,010, filed Feb. 23, 2010, issued as U.S. Pat. No. 8,792,951 on Jul. 29, 2014. These applications are incorporated by reference along with all other references cited in this application.

BACKGROUND OF THE INVENTION

The human skeletal system provides many different and important functions. The skeletal system gives a body its shape, allows people to stand, gives support for movements such as walking, running, and jumping, and protects the various organs. For example, the vertebral column supports the upright position of the person and protects the spinal cord. The ribs protect the lungs and heart. The pelvis protects the intestines.

In addition to support, protection, and movement, bones are also responsible for many physiological processes such as blood cell formation and maintaining blood calcium. Bone marrow, which can be found in certain types of bone tissue, is responsible for the creation of erythrocytes (i.e., red blood cells), leukocytes (i.e., white blood cells), and platelets. Certain bone cells are responsible for maintaining normal blood calcium levels. Calcium is used for muscle contraction, metabolism, nerve impulses, and the formation of blood clots.

Thus, bones play an important role in people's well-being. However, there are few, if any, systems and techniques for objectively measuring the health of bone. In most cases, the determination of the health of a bone is subjective. A physician weighs factors such as the patient's age, whether or not the patient smokes, medications that the patient takes, current or past health problems (e.g., cardiovascular disease, asthma, and diabetes), and so forth. After weighing the factors, the physician develops an opinion of the health of the bone. This opinion is then used to guide medical decisions or actions. For example, if a healthy bone is broken, the doctor may recommend one course of action. If an unhealthy bone is broken, the doctor may recommend a different course of action.

However, different physicians may disagree on the health of the bone since the determination of bone health is subjective. Thus, one physician may recommend one course of action for a patient and another physician may recommend a different course of action for the same patient.

Therefore, there is a need for systems and techniques for making objective measurements for bone so that medical decisions are more consistent with the actual health of the bone.

BRIEF SUMMARY OF THE INVENTION

A bone oximeter probe includes an elongated member and a sensor head at an end of the elongated member to make measurements for a bone. The measurements can indicate the viability or nonviability of the bone. In an implementation, the probe is advanced through an incision in soft tissue, towards the underlying bone, and positioned so that the sensor head faces the bone to be measured. Optical signals are sent from the sensor head and into the bone. The bone reflects some of the optical signals which are then detected (e.g., received or collected) so that measurements for the bone can be made. Some of these measurements include an oxygen saturation level value, and a total hemoglobin concentration value of the bone.

In a specific implementation, a method of making an oxygen saturation measurement for a bone includes advancing an elongated probe through an incision in a tissue, where the probe includes a first tube, a sensor head, connected to the first tube, and first and second fiber optic cables, connected to the sensor head. The ends of the first and second fiber optic cables are exposed on a surface of the sensor head and an axis passing through the first tube passes through the surface.

The method further includes positioning the elongated probe in the tissue so the sensor head contacts a bone for which an oxygen saturation parameter is to be measured and causing transmitting of a first light signal through the first fiber optic cable to the sensor head. From the sensor head, the first light signal is directed at the bone. Further, after causing transmitting of the first light signal through the first fiber optic cable, the method includes maintaining a position of the probe at the bone for the probe to receive a reflection of the first light signal from the bone. The reflection of the first light signal from the bone is a second light signal. The method also includes causing transmitting of the second light signal via the second fiber optic cable. The second light signal is transmitted in a direction opposite of the transmitting of the first light signal.

The sensor head may include a first source opening, where the first fiber optic cable is connected to the first source opening, and a first detector opening, where the second fiber optic cable is connected to the first detector opening. In a specific implementation, a distance between the first source opening and the first detector opening is about 3.5 millimeters or less. The surface of the sensor head may have a surface area of about 24 square millimeters or less.

The probe may further include a second tube, extending from a proximal end of the first tube to a connector for connecting the probe to a console, where the second tube includes a flexible material and the first tube includes a rigid material.

In a specific implementation, the method further includes connecting a connector of the probe to a console including an electronic display, after causing transmitting of the first light signal through the first fiber optic cable and causing transmitting of the second light signal via the second fiber optic cable, causing a calculation in the console of an oxygen saturation parameter associated with the first light signal and second light signal, and causing displaying of the oxygen saturation parameter on the electronic display. The oxygen saturation parameter may include at least one of an oxygen saturation level value of the bone or a total hemoglobin concentration value of the bone that was measured.

In an implementation, the fiber optic cables extend through a passageway within the probe to the sensor head. The sensor head may include a first source structure, a second source structure, a first detector structure, where the first detector structure includes the second fiber optic cable, and a second detector structure. A first distance extends between the first source structure and the first detector structure without touching another source or detector structure, a second distance extends between the second source structure and the second detector structure without touching another source or detector structure. The first distance is different from the second distance.

In another implementation, the sensor head includes a first source structure including the first fiber optic cable, a second source structure, a first detector structure including the second fiber optic cable, and a second detector structure. The first source structure, second source structure, first detector structure, and second detector structure are arranged on a line and the axis is perpendicular to the line.

The sensor head may include a first source structure including the first fiber optic cable, and a first detector structure including the second fiber optic cable. In a specific implementation, an edge defines the surface of the sensor head and distances between the first source structure and the edge and between the first detector structure and the edge are about 1.5 millimeters or less.

In a specific implementation, the positioning the elongated probe in the tissue includes positioning the elongated probe in the tissue so the sensor head contacts a first location on the bone. The method further includes after the causing transmitting of the second light signal, reading a first signal quality value on an electronic display of a console, repositioning the elongated probe in the tissue so the sensor head contacts a second location on the bone, different from the first location, and after the repositioning the elongated probe, reading a second signal quality value on the electronic display of the console.

In a specific implementation, a medical device includes a probe for making an oxygen saturation measurement for a bone. The probe includes a rigid elongated member such as a rigid tube or a solid rod. The elongated member includes a proximal end, and a distal end, opposite the proximal end. The probe also includes a sensor head, connected to the distal end of the elongated member, where the sensor head includes first and second openings, and first and second fiber optic cables. The first fiber optic cable is connected to the first opening. The second fiber optic cable is connected to the second opening. The sensor head is positioned so that light directed into the bone via the first fiber optic cable travels in a first direction from the proximal end towards the distal end and exits the first opening in the first direction. And light reflected from the bone enters the second opening in a second direction, and travels from the distal end towards the proximal end in the second direction and through the second fiber optic cable.

The probe further includes a flexible tube, extending from the proximal end of the elongated member, and a connector, connected to the flexible tube.

The medical device may further include a beam combiner, external to the probe. The beam combiner may include a first input connected to a first radiation source of a first wavelength and a second input connected to a second radiation source of a second wavelength, different from the first wavelength. In an implementation, the first fiber optic cable is connected to the beam combiner and outputs light of the first wavelength and light of the second wavelength.

The beam combiner may output light of the first wavelength at a first time, and output light of the second wavelength at a second time, different from the first time.

In a specific implementation, a surface of the sensor head including the first and second openings is curved concave to complement a convex portion of the bone to be measured. In another implementation, the surface is curved convex to complement a concave portion of the bone to be measured.

In a specific implementation, a method for making a bone oximeter probe having a pad to conform to a surface of a bone to be measured, includes attaching the pad to a block, and creating a set of channels through the pad and block. Each channel extends through the pad and block, from a front surface of the pad to a back surface of the block, opposite the front surface. The method further includes threading a fiber optic cable into each channel of the set of channels, positioning the fiber optic cable within each channel so that an end of the fiber optic cable is flush with the front surface of the pad, attaching the fiber optic cable to the channel, and attaching the block to a distal end of a rigid tube. At least a portion of the pad protrudes out from the distal end.

In a specific implementation, the attaching the block to a rigid tube includes inserting an opposite end of the fiber optic cable into the distal end of the rigid tube, advancing the fiber optic cable through a passageway in the rigid tube so that the opposite end of the fiber optic cable exits a proximal end of the rigid tube, opposite the distal end, applying an adhesive to at least one of the block or the passageway, and inserting the block into the distal end of the rigid tube. During the attaching the fiber optic cable to the channel, a portion of the fiber optic cable may be lying within a passageway of the rigid tube.

In a specific implementation, a bone oximeter probe includes a hollow tube, and a sensor unit. The sensor unit is connected to a distal end of the hollow tube. The sensor unit includes a block and a pad, connected to the block, to conform to surface contours of a bone to be measured. There are first and second channels extending through the block and pad to a surface of the pad and first and second fiber optic cables. The first fiber optic cable is connected to the first channel and terminates within the first channel before reaching the surface of the pad. The second fiber optic cable is connected to the second channel and terminates within the second channel before reaching the surface of the pad.

The first and second fiber optic cables may extend from a proximal end of the hollow tube, opposite the distal end, and into the pad without changing direction. The pad may include foam. The sensor unit may be inside the hollow tube.

The bone oximeter system can be used to measure StO2, Hgb, or both of human bone. In a specific implementation, the sensor or sensor head of the bone oximeter probe is placed on a bone surface, instead of soft tissue. StO2 measurements can be made for any bone, including nonhuman bones. Some specific examples of bones for which measurements can be made include bovine long bone, the spinous process of a pig, the skull of a pig, and the human fibular. The measurements may or may not be used in spine surgery (e.g., spine fusion surgery). The bone oximeter probe typically has a very small sensor head to accommodate the small surface of, for example, the spinous process or transverse process.

In a specific implementation, hypoxic changes in bone are detected and continuously monitored with the sensor head when the sensor head is in direct contact with the bone surface. StO2 differences between normal and hypoxic bone may be on the order of about or of at least 15-20 percentage points, thus, StO2 is detectable. The differences may be seen in about 20 minutes.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 15 shows a side view of a bone oximeter probe with sensor openings on a sidewall of the probe.

FIG. 16 shows a longitudinal cross-sectional view of the tip of the probe shown in FIG. 15 containing optical fibers, forming a side-looking sensor array.

FIG. 17 shows a longitudinal cross-sectional view of another probe with both a forward-looking sensor array and a side-looking sensor array.

DETAILED DESCRIPTION OF THE INVENTION

Figure 1:
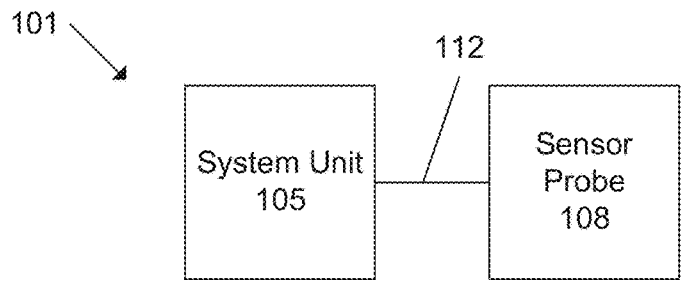
FIG. 1 shows a block diagram of a system for obtaining optical measurements of tissue in a patient.

FIG. 1 shows a system 101 for measuring various parameters of a tissue in a patient. The parameters of the tissue measured by the system may include an oxygen saturation level, a total hemoglobin concentration, a blood flow, a pulse, and a signal level of light reflected from the tissue. The system includes a system unit 105 and a sensor probe 108, which is connected to the system unit via a wired connection 112. Connection 112 may be an electrical, optical, or another wired connection including any number of wires (e.g., one, two, three, four, five, six, or more wires or optical fibers), or any combination of these or other types of connections. In other implementations of the invention, however, connection 112 may be wireless such as via a radio frequency (RF) or infrared communication.

Typically, the system is used by placing the sensor probe in contact or close proximity to tissue (e.g., bone or skin or internal organ or tissue) at a site where tissue parameter measurements are desired. The system unit causes an input signal to be emitted by the sensor probe into the tissue (e.g., human tissue). There may be multiple input signals, and these signals may have varying or different wavelengths. The input signal is transmitted into or through the tissue.

Then, after transmission through or reflection off the tissue, the signal is received at the sensor probe. This received signal is received and analyzed by the system unit. Based on the received signal, the system unit determines various parameters of the tissue—an oxygen saturation level, a total hemoglobin concentration, a blood flow, a pulse, a signal level of light reflected from the tissue. One or any combinations of these parameters can be displayed on a display screen of the system unit.

In an implementation, the system is a tissue oximeter, which can measure oxygen saturation and hemoglobin concentration, without requiring a pulse or heart beat. A tissue oximeter of the invention is applicable to many areas of medicine and surgery including plastic surgery and spinal surgery. The tissue oximeter can make oxygen saturation and hemoglobin concentration measurements of tissue where there is no pulse; such tissue, for example, may have been separated from the body (e.g., a flap) and will be transplanted to another place in the body.

Aspects of the invention are also applicable to a pulse oximeter. In contrast to a tissue oximeter, a pulse oximeter bases measurements on a pulse. A pulse oximeter typically measures the absorbance of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, and 7,247,142. These patents are assigned to the same assignee as this patent application and are incorporated by reference along with all other references cited in this application.

In an implementation, the system is a laser Doppler flow meter, which can measure a blood flow, a pulse rate, or both in the tissue. In principle, this technique involves directing a laser beam (e.g., through optical fibers) onto a part of the tissue and receiving, with the aid of an appropriate detector, part of the light scattered and reflected back by that part of the tissue that is irradiated by the laser beam. When light hits moving blood cells, the light undergoes a change in wavelength, which may be referred to as a Doppler shift, while light hitting nonmoving tissue is unchanged. The magnitude and frequency distribution of these changes in wavelength are directly related to the number and velocity of blood cells but unrelated to their direction of movement. This information is captured by returning optical fibers in the sensor probe, converted into an electrical signal and analyzed.

In an implementation, the system is both a tissue oximeter and laser Doppler flow meter. Therefore, the system can simultaneously determine multiple parameters of a tissue, which may include a signal level of returned light, oxygen saturation level, total hemoglobin concentration, blood flow, pulse rate, and others.

Figure 2:
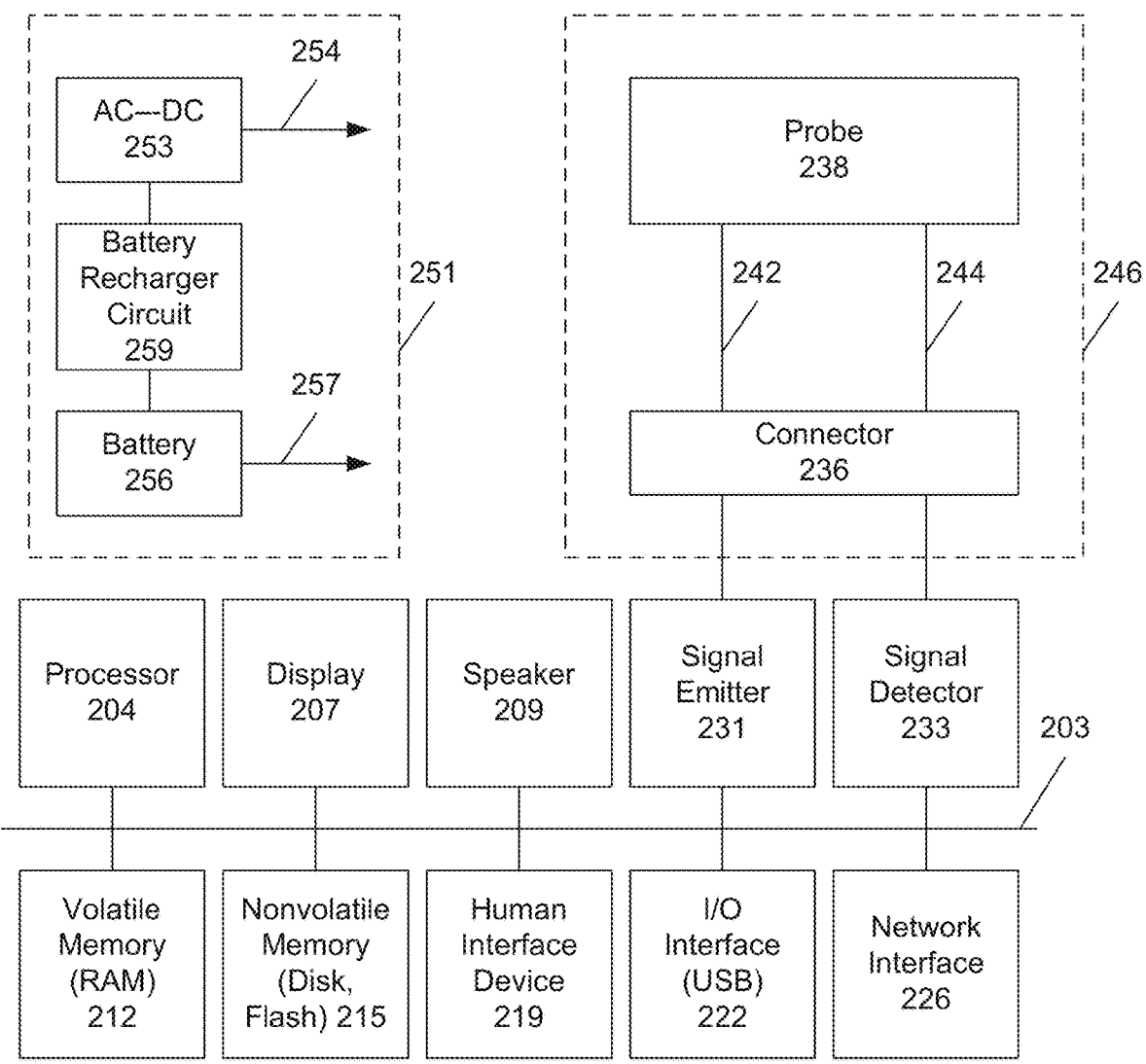
FIG. 2 shows a more detailed block diagram of a specific implementation of the system of FIG. 1.

FIG. 2 shows greater detail of a specific implementation of the system of FIG. 1. The system includes a processor 204, display 207, speaker 209, signal emitter 231, signal detector 233, volatile memory 212, nonvolatile memory 215, human interface device or HID 219, I/O interface 222, and network interface 226. These components are housed within a system unit enclosure. Different implementations of the system may include any number of the components described, in any combination or configuration, and may also include other components not shown.

The components are linked together using a bus 203, which represents the system bus architecture of the system. Although this figure shows one bus that connects to each component, the busing is illustrative of any interconnection scheme serving to link the subsystems. For example, speaker 209 could be connected to the other subsystems through a port or have an internal direct connection to processor 204.

A sensor probe 246 of the system includes a probe 238 and connector 236. The probe is connected to the connector using wires 242 and 244. The connector removably connects the probe and its wires to the signal emitter and signal detectors in the system unit. There is one cable or set of cables 242 to connect to the signal emitter, and one cable or set of cables 244 to connect to the signal detector. In an implementation the cables are fiber optic cables, but in other implementations, the cables are electrical wires. In yet another implementation, the cables include both fiber optic cables and electrical wires.

Signal emitter 231 is a light source that emits light at one or more specific wavelengths. In a specific implementation, two wavelengths of light (e.g., 690 nanometers and 830 nanometers) are used. In other implementations, other wavelengths of light may be used. The signal emitter is typically implemented using a laser diode or light emitting diode (LED). Signal detector 233 is typically a photodetector capable of detecting the light at the wavelengths produced by the signal emitter.

Connector 236 may have a locking feature; e.g., insert connector, and then twist or screw to lock. If so, the connector is more securely held to the system unit and it will need to be unlocked before it can be removed. This will help prevent accidental removal of the probe.

The connector may also have a first keying feature, so that the connector can only be inserted into a connector receptacle of the system unit in one or more specific orientations. This will ensure that proper connections are made.

The connector may also have a second keying feature that provides an indication to the system unit which type of probe is attached. The system unit may handle making measurements for a number of different types of probes. When a probe is inserted, the system uses the second keying feature to determine which type of probe is connected to the system. Then the system can perform the appropriate functions, use the proper algorithms, or otherwise make adjustments in its operation for the specific probe type.

For example, when the system detects a probe with two optical fiber ends at its scanning surface is connected, the system uses probe algorithms and operation specific for the two optical fiber probe. When the system detects that a probe with four optical fiber ends at its scanning surface is connected, the system uses probe algorithms and operation specific for the four optical fiber probe. When the system detects that a probe in a dilator is connected, the system uses dilator probe algorithms and operation. When the system detects that a probe in a hollow needle is connected, the system uses needle probe algorithms and operation. A system can handle any number of different types of probes. There may be different probes for measuring different parts of the body, or different sizes or versions of a probe for measuring a part of the body.

With the second keying feature, the system will be able to distinguish between the different probes. The second keying feature can use any type of coding system to represent each probe including binary coding. For example, for a probe, there are four second keying inputs, each of which can be a logic 0 or 1. With four second keying inputs, the system will be able to distinguish between sixteen different probes.

Probe 246 may be a handheld tool and a user moves the probe from one point to another to make measurements. However, in some applications, probe 246 is part of an endoscopic instrument, robotic instrument, a part of an instrument that inserts inside a body, or any combination of these. For example, the probe is moved or operated using a guiding interface, which may or may not include haptic technology.

In various implementations, the system is powered using a wall outlet or battery powered, or both. Block 251 shows a power block of the system having both AC and battery power options. In an implementation, the system includes an AC-DC converter 253. The converter takes AC power from a wall socket, converts AC power to DC power, and the DC output is connected to the components of the system needing power (indicated by an arrow 254). In an implementation, the system is battery operated. The DC output of a battery 256 is connected to the components of the system needing power (indicated by an arrow 257). The battery is recharged using a recharger circuit 259, which received DC power from an AC-DC converter. The AC-DC converter and recharger circuit may be combined into a single circuit.

The nonvolatile memory may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive), battery-backed-up volatile memory, tape storage, reader, and other similar media, and combinations of these.

The processor may include multiple processors or a multicore processor, which may permit parallel processing of information. Further, the system may also be part of a distributed environment. In a distributed environment, individual systems are connected to a network and are available to lend resources to another system in the network as needed. For example, a single system unit may be used to collect results from numerous sensor probes at different locations.

Aspects of the invention may include software executable code or firmware (e.g., code stored in a read only memory or ROM chip). The software executable code or firmware may embody algorithms used in making oxygen saturation measurements of the tissue. The software executable code or firmware may include code to implement a user interface by which a user uses the system, displays results on the display, and selects or specifies parameters that affect the operation of the system.

Further, a computer-implemented or computer-executable version of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). The mass storage device may be accessible via an Internet connection at a remote server (which may be referred to as being stored on the "cloud"). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, Matlab (from MathWorks, www-.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows 95, 98, Me, Windows NT, Windows 2000, Windows XP, Windows XP x64 Edition, Windows Vista, Windows 7, Windows CE, Windows Mobile), Linux, HP-UX, UNIX, Sun OS, Solaris, Mac OS X, Google Chrome, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may interface to other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or other device (e.g., laptop computer, smartphone, or personal digital assistant), a user accesses a system of the invention through a network such as the Internet. The user will be able to see the data being gathered by the machine. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 3:
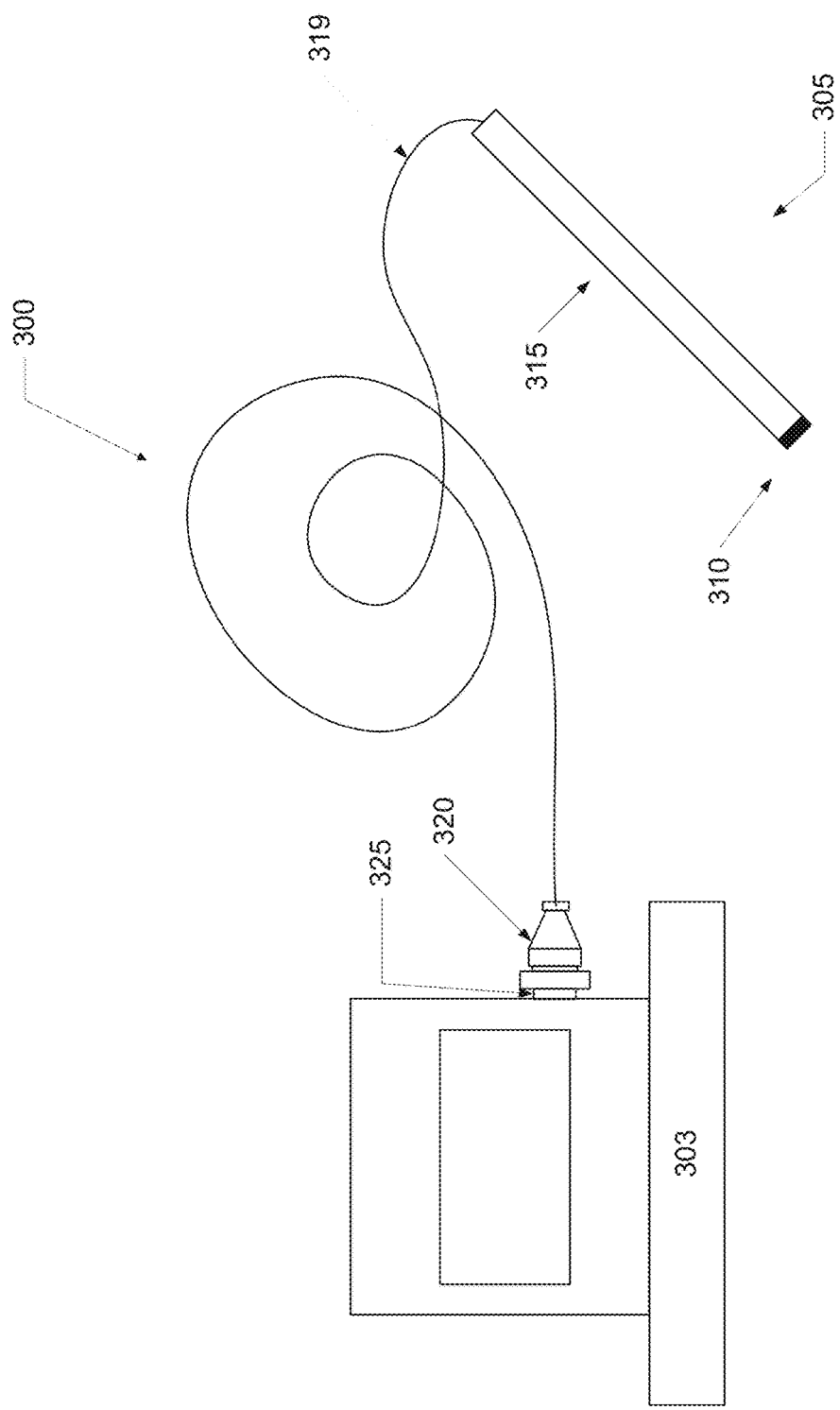
FIG. 3 shows a system of the invention including a monitoring console and a bone oximeter probe connected to the console.

FIG. 3 shows one implementation of a system 300 which includes a monitoring console 303 and a bone oximeter probe 305. The bone oximeter probe includes a sensor head or unit 310 connected to an elongated member 315 connected to a cable 319. The sensor head includes one or more distal ends of conductors (e.g., optical fibers, electrical wires, or both) which are located at a tip of the probe. The probe also includes a connector 320 which includes proximal ends of the conductors. The conductors or optical fibers extend from the connector, through a passageway within the probe (i.e. within the cable and elongated member), to the sensor head. The connector is removably attached to a receptacle 325 which is affixed to or mounted on the monitoring console.

To use this probe to make measurements for a bone, a user, such as a physician or surgeon, holds the elongated member and positions the sensor head to face or contact the bone to be measured. A signal is transmitted from the monitoring console, through the conductors, out the sensor head, and into the bone. The bone reflects a portion of the signal which is received at the sensor head and transmitted through the conductors to the console. The console makes a calculation based on the signal and reflected signal to determine a bone measurement. The bone measurement can then be displayed on an electronic display of the console. In a specific implementation, the bone measurement is an oxygen saturation parameter. The oxygen saturation parameter may be an oxygen saturation level value of the bone, a total hemoglobin concentration value of the bone, or both.

Generally, the oxygen saturation parameter provides an indication of the health or vitality of the bone. The surgeon can then decide on a specific course of action based on the health or oxygen saturation parameter of the bone. For example, in head and neck cancer surgery, tumors that occur in the jaw bone (i.e., oral cancers) may be radiated and then resected. However, nonviable bone (often caused by radiation treatment damage, known as radioosteonecrosis) is typically removed along with the tumor. Removal of the nonviable bone may help to prevent, for example, infections. Therefore, information on what regions of the bone are nonviable can lead to reduced postoperative complications. In other words, the oxygen saturation measurements provided by the system can help the surgeon determine the viable and nonviable regions of the bone so that the surgeon knows what specific portion of bone should be resected.

Further, a surgeon may also remove a portion of the healthy bone surrounding the tumor or diseased bone to minimize the risk of possible seeding. Seeding refers to the spreading of cancerous cells during tumor removal. Using this bone oximeter, the surgeon can determine where the diseased bone ends and the healthy bone begins. The surgeon can then resect the tumor along with a portion of the healthy bone that surrounds the tumor.

The probe can be made of any suitable biocompatible material. The term "biocompatible material" is used in this application in its broadest sense and refers to a material which is used in situations where it comes into contact with the cells, bodily fluids, or both of living animals and humans. It is desired that the selected biocompatible material is chemically inert, and thermally and mechanically stable. A probe can be made of a metal (e.g., stainless steel, aluminum, and others), a polymeric material, ceramic, plastic, or combinations of these.

In a specific implementation, the elongated member and sensor unit of the probe is made of metal. Some examples of metals include aluminum (e.g., 6061 aluminum), steel, stainless steel, and titanium. The elongated member can be a tube (e.g., aluminum tube) that is hollow or has a passageway to contain the conductors.

Sensor unit 310 includes distal ends of conductors such as optical fibers. The distal ends of the conductors are arranged in a particular pattern (which are described more in detail in FIGS. 7 through 12), and may include at least one source structure and at least one detector structure. A source structure is a structure in the sensor head that provides and transmits light into the bone or other tissue. The source structure can generate light, or it can be a structural component that transmits light generated elsewhere (e.g., from an upstream source). A detector structure is a structure in the sensor unit that detects light (or that is a structural component of the detection process) which is scattered and reflected from the bone.

In one embodiment, a source structure can be a laser or light emitting diode (LED) that emits a light of a specific wavelength suitable to monitor oxygen saturation. A detector structure can be a photodiode (e.g., a PN diode, a PIN diode, or an avalanche diode) that detects the light transmitted and reflected from a bone, after the source structure emits the light into the bone. In a sensor unit, both LEDs and photodiodes can be located at the scanning surface of the sensor unit. These LEDs and photodiodes can then be electrically connected to a system unit or console. In this embodiment, since the light is generated next to the bone surface and subsequently detected at the bone surface, there is less attenuation of a signal as compared to other implementations where the LEDs and photodiodes are at the console.

In another embodiment, a source structure is an opening in a sensor unit (at its scanning surface) with an optical fiber inside, which is connected to an emitter located elsewhere (e.g., system unit). Likewise, a detector structure is an opening in a sensor unit (at its scanning surface) with an optical fiber inside, which is connected to a detector located elsewhere. The optical fibers from each sensor unit are then connected to either an emitter or a detector which may be located in a system unit or console.

This design can lower the cost of the probe because the emitters (e.g., LEDs) and photodiodes are not a part of the probe. Rather, the emitters and photodiodes are external to the probe. Thus, the probe can be made to be disposable and be cost-effectively replaced when it becomes contaminated such as after use (e.g., after one use).

In various other embodiments, a probe can have emitters and no photodiodes, a probe can have photodiodes and no emitters, a probe can have emitters and photodiodes, a probe can have some emitters while other emitters are external to the probe, or a probe can have some photodiodes while other photodiodes are external to the probe.

In embodiments of the invention, the cable contains conductors (e.g., optical fibers) in a cable jacket and connects the sensor unit to a connector which couples a sensor probe to a monitoring console. The length of the cable may vary. In a specific implementation, the length of the cable is about 3 meters, but can range from about 1.2 meters to about 6 meters. For example, the cable may be about 1.5, 2, 2.5, 2.6, 2.7, 2.8, 2.9, 3, 3.1, 3.2, 3.3, 3.4, 3.5, 3.6, 3.7, 3.8, 3.9, 4, 4.5, 5, 5.5, or 5.9 meters or more than 6 meters. Depending on the specific application, the cable length may be less than 1.2 meters. In some applications, the cable length will be greater than 6 meters. It may be desirable to use longer cables when a patient's immune system is compromised and needs to be kept away from sources of contamination, such as a console.

In an implementation, the cable includes one or more optical wave guides enclosed in a flexible cable jacket. The optical wave guides may be used to transmit light from the console, through the sensor unit and into the bone. The optical wave guides may also be used to transmit the light received from the bone back to the console.

The optical wave guides may have the shape of a polygon, such as a square, rectangle, triangle, or other shape. In other cases, the optical wave guides may have circular or oval shapes. In a specific implementation, the optical wave guides are multiple strands of fiber optic cable or optical fiber. The flexible cable jacket may be made of polyvinyl chloride (PVC) such as thin-walled PVC with or without an aluminum helical monocoil, shrink wrap tubing, plastic, rubber, or vinyl.

In a specific embodiment, all of the fiber optic cables are enclosed within one end, or both ends of the flexible cable jacket. Minimizing the number of exposed cables lowers the likelihood that the cables will get entangled. In another embodiment, the fiber optic cables are not enclosed together and instead each fiber optic cable is enclosed in its own flexible cable jacket.

In a specific implementation, the cable is passive. For example, it will not contain any active, generative properties to maintain signal integrity. However, in other implementations, the cable may include active components. The cable may include active components to amplify the signal transmitted through the sensor unit, received at the sensor unit, or both. For example, long lengths of cable subject to significant attenuation may benefit from amplification. Amplification may also be used if the monitored site contains a particularly dense structure such as bone. In a specific implementation, radiation sources such as light emitting diodes (LEDs) may be placed in the sensor unit. Thus, the cable may contain electrical wiring to transmit power to the radiation sources.

In an embodiment of the invention, each opening on the sensor unit and corresponding cable is dedicated to a particular purpose. For example, a first opening on the sensor unit (and corresponding fiber optic cable) is dedicated to transmitting light from the monitoring console. A second opening on the sensor unit is dedicated to transmitting a signal received at the second opening to the monitoring console.

Some embodiments use a particular opening and cable for multiple purposes (e.g., both input and output) using a scheme such as multiplexing.

In a specific embodiment, a particular opening and cable transmits an output to affect a reaction (e.g., sending electrical signals to stimulate muscle, nerve, or other tissue). Another opening and cable transmits the resultant signal back to the monitoring device. In yet another embodiment, the openings and cables may simply detect changes and transmit these changes back to the monitoring device. For example, the openings and cables may carry voltage changes in the patient's tissue back to the monitoring device.

Connector 320 at the end of the cable attaches the sensor probe to its receptacle on the console. The connector also protects the cable from accidental disconnection. The connector may include a collar that threads onto the receptacle on the console. Alternatively, the connector may include a lug closure, press-fit, or snap-fit components.

In a specific implementation, the console can provide alerts to the user when a proper connection is made between the sensor probe and the console. The alerts may be visual (e.g., a flashing light on a display of console), audible, or both. The display monitor may also show a type of sensor device (e.g., bone oximeter device, dilator sensor device, needle sensor device, and others) that is attached to the console, as well as other information.

In a specific implementation, there may be other connectors on the cable besides connector 320. These other connectors allow the cable to be separated into two or more pieces. Additional lengths of cable can be added to one or both pieces to increase the overall length of the cable or portions of the cable can be removed to shorten the overall length of the cable. Furthermore, having multiple connectors allows disconnecting of a contaminated portion of the cable from an uncontaminated portion of the cable. The contaminated portion of the cable, rather than the entire length of cable, can be disposed and new cable can then be connected to the uncontaminated portion of the cable. This can save money because the entire length of the cable is not being discarded after one-use.

In one implementation, console 303 (sometimes referred to as a monitoring console or system unit) shown in FIG. 3 can be a portable console which may be hand carried. A portable console can follow a patient and optical measurements can be made anywhere in the hospital. In this implementation, it is desirable that the portable console is battery operated. In another implementation, the console may be a large, nonportable device that is attached to a wall or secured to a stand. In this implementation, the system is typically connected to AC power.

The console may include a mass storage device to store data. Mass storage devices may include mass disk drives, floppy disks, magnetic disks, optical media, phase-change media, fixed disks, hard disks, CD-ROM and CD-RW drives, DVD-ROM and DVD-RW drives, flash and other nonvolatile solid-state storage drives, tape storage, reader, and other similar devices, and combinations of these.

The stored data may include patient information. This includes, for example, the patient's name, social security number, or other identifying information, measurements of light returned from the patient's tissue, oxygen saturation, total hemoglobin concentration, blood flow, pulse, signal quality, and the time and date of measurements. The measurements of various physiological parameters may include high, low, and average values and elapsed time between measurements.

The above drives may also be used to update software in the console. The console may receive software updates via a communication network such as the Internet.

In an implementation, the console also includes an interface for transferring data to another device such as a computer. The interface may be a serial, parallel, universal serial bus (USB) port, RS-232 port, printer port, and the like. The interface may also be adapted for wireless transfer and download, such as an infrared port. The system transfers data without interruption in the monitoring of the patient.

The console also includes a display screen (e.g., electronic display) which may display the patient's data, such as measurements of light returned from the patient's tissue, oxygen saturation, total hemoglobin concentration, blood flow, pulse, signal quality, or any combinations of these parameters. The screen may be a flat panel display or include a touch screen interface so that the user can input data into the console.

The console, in addition to the display, may also include a processor, signal emitter circuit, signal detector circuit, and a receptacle to removably couple ends of one or more conductors. In a specific implementation, the ends of one or more conductors (e.g., optical fibers or electrical wires) are instead permanently connected to the console. The signal emitter circuit may operate to send a signal through the one or more conductors. The signal detector circuit then receives a signal via one or more conductors.

In a specific implementation, the signal emitter circuit may include one or more laser emitters, light emitting diode (LED) emitters, or both. The signal emitter circuit may be used to generate an optical signal having two or more different wavelengths to be transmitted through the sensor unit. The wavelengths may range from about 600 nanometers to about 900 nanometers.

In a specific implementation, the console includes first and second radiation sources. The radiation sources may be dual wavelength light sources. That is, the first and second radiation sources each provide two wavelengths of radiation. The first radiation source, second radiation source, or both may include one or more laser diodes or light emitting diodes (LEDs) that produce light in any wavelength, but typically the wavelengths range from about 600 nanometers to about 900 nanometers. In a specific implementation, the first and second radiation sources generate a first wavelength of light that is about 690 nanometers and a second wavelength of light that is about 830 nanometers.

In a specific implementation, one or more near-infrared radiation sources are included within the console. In other implementations, the radiation sources may be external to the console. For example, the radiation sources may be contained within a separate unit between the console and sensor probe. The radiation sources may, for example, be contained in a sensor probe or sensor unit itself or in other parts (e.g., in the console). In yet another implementation, some radiation sources may be within the console while other radiation sources are external to the console.

These radiation sources may be near-infrared lasers. In a specific implementation, there is one near-infrared laser located within the console. In other implementations, there may be more than one near-infrared laser. For example, there may be 2, 3, 4, 5, 6, 7, 8, 9, or 10, or more than 10 radiation sources. In another implementation, the radiation sources may include those that produce a visible light.

Also, in a specific implementation only a percentage of the power output of the source is transmitted to the tissue. For example, when the laser diode output is 30 milliwatts, the power that gets to the tissue may be about 3 milliwatts. So, approximately 1/10 of the power of the laser diode is transmitted into the tissue.

In a specific implementation, a single pulse of light is transmitted into the tissue. In another implementation, multiple pulses of light may be transmitted into the tissue. For example, a first pulse of light may be received by a first detector. A second pulse of light may be received by a second detector.

Figure 4:
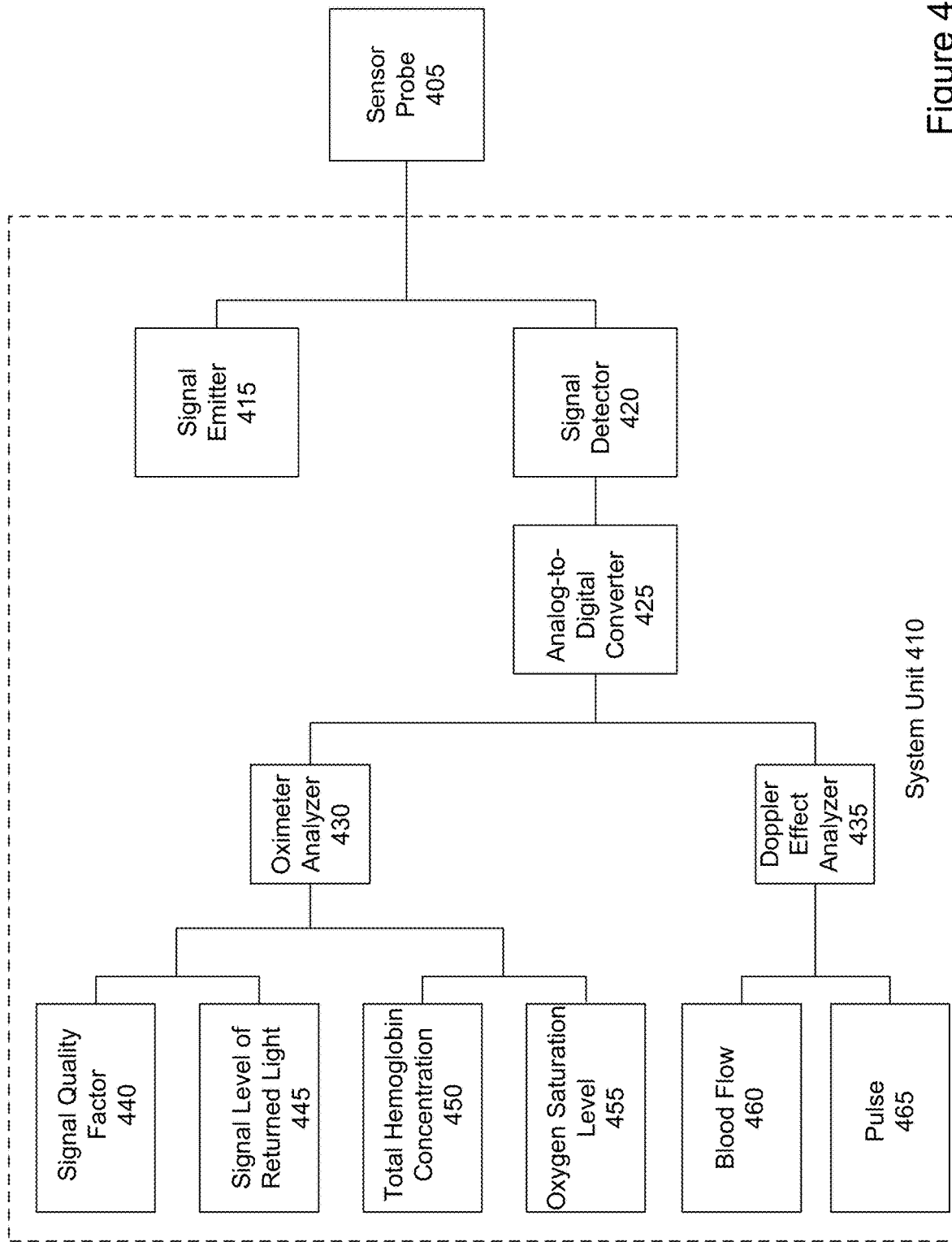
FIG. 4 shows a block diagram of a system where various parameters of bone contacted by a sensor probe can be measured and calculated to determine an indicator of bone health.

FIG. 4 shows a specific implementation of a measuring or monitoring system in accordance with the present invention. As shown, a sensor probe 405 (e.g., a sensor probe which is a part of a bone oximeter device) is connected to a system unit 410. The system unit includes a signal emitter 415, a signal detector 420, an analog-to-digital converter 425, an oximeter analyzer 430, a Doppler effect analyzer 435, and a number of output parameters. These output parameters include a signal quality factor 440, a signal level of returned light 445, a total hemoglobin concentration 450, an oxygen saturation level 455, a blood flow 460, and a pulse 465.

These components may be housed within a single housing. Alternatively, these components may be housed in separate housings. Different implementations of the system may include any number of the components described, in any combination or configuration, and may also include other components not shown.

Signal emitter 415 emits light of a suitable wavelength or wavelengths into sensor probe 405 through source fibers into a bone where optical measurements are desired. When light is transmitted to a target bone via source structures in the sensor unit, light scatters due to the heterogeneous structure of the bone, and some of the light is absorbed by chromophores such as hemoglobin. An attenuated version of the light that is reflected by the bone is detected by detector structures in the sensor unit and is transmitted to signal detector 420 in the system unit. Also, due to Doppler effect, the frequency of the reflected light is broadened and the frequency of the reflected light will be broader than the frequency spectrum of the original light. These changes are also detected by signal detector 420. As shown in FIG. 4, signal detector 420 may be connected to analog-to-digital converter 425 which in turn may be connected to oximeter analyzer 430, Doppler effect analyzer 435, or both.

From optical measurements obtained from the signal detector, a signal quality factor 440 (sometimes referred to as a Q factor in other applications) can be obtained. The signal quality factor is a parameter that is associated with the ratios of optical measurements from the sensor head. The calculated signal quality factor can vary from 0 to 1 (sometimes scaled and displayed from 0 to 100). When the signal quality factor is approximately 1 (or 100 when scaled up), this indicates that the sensor unit is in good contact with bone, that the bone is highly homogeneous, and that the sensor probe is in good working order. The signal quality factor can indicate the quality of signal obtained from the signal detector. Discussions of a Q factor or a signal quality factor can be found in U.S. patent application Ser. No. 11/162,380, filed Sep. 8, 2005, which is incorporated by reference.

The changes in the intensity and frequency spectrum of returned light is analyzed by oximeter analyzer 430 and Doppler effect analyzer 435. From these analyses, a number of different parameters can be calculated. One or combinations of parameters will help a surgeon to determine the health of the tissue or bone.

Oximeter analyzer 430 calculates oxygen saturation level or value ($StO_2$) 455, hemoglobin concentration (deoxyhemoglobin, oxyhemoglobin, or total hemoglobin) 450, or both. The calculations are based on a value of the initial light generated by the signal emitter and a value of an attenuated version of the light that is reflected from the bone and is subsequently detected by the signal detector. The term oxygen saturation level (or value) refers to the percentage of hemoglobin that is bound to oxygen at the time of measurement. Additional details on attenuation methods are also discussed in U.S. patent application Ser. No. 12/126,860, filed May 24, 2008, which is incorporated by reference. The attenuation ratio method may also include techniques discussed in U.S. Pat. No. 6,587,701, which is incorporated by reference.

In the automatic error-cancellation or self-calibration scheme, the system factors such as source intensity, detector gain, and loss of light in the optical fibers and connectors are cancelled automatically. The automatic error-cancellation scheme is discussed in more detail as equations 5a and 5b in U.S. Pat. No. 6,597,931, which is incorporated by reference. The self-calibration scheme may also include equations discussed in U.S. Pat. Nos. 6,516,209, 6,735,458, and 6,078,833, U.S. patent application Ser. No. 12/126,860, filed May 24, 2008, and *New Optical Probe Designs for Absolute (Self-Calibrating) NIR Tissue Hemoglobin Measurements*, Proc. SPIE 3597, pages 618-31 (1999), which are incorporated by reference.

Generally, bones, like other tissues, use the oxygen and nutrients that blood supplies. Healthy bones can be distinguished from unhealthy bones using the sensor measurements provided by the system. For example, unhealthy bones can have inadequate blood perfusion. Thus, an indication of bone health can be determined by measuring bone oxygenation. Specifically, healthy bones can have a higher number of blood cells (and thus a higher concentration of hemoglobin) and be more richly oxygenated as compared to unhealthy bones.

The signal level of returned light can be used as an indicator of whether a bone is healthy or unhealthy. A healthy bone or a bone that is well-perfused will absorb infrared and visible red light more than the unhealthy bone.

In a specific implementation, the system includes a laser Doppler to detect regions of high versus low blood flow. Such information can indicate whether or not perfusion is adequate (e.g., bony bleeding). Doppler effect analyzer 435 can calculate blood flow 460 and pulse 465. The Doppler effect analyzer analyses the intensity and spectrum change of light when it is transmitted and reflected from a bone. Laser light is scattered by the red blood cells in the capillaries and the tissue surrounding the capillaries. The velocity of the blood flow, which runs in all directions in the capillary network, has velocity distribution averaging at 1 millimeter per second or less. The tissue scattering cross section is much greater than that of the moving red blood cells. Based on this information, the following calculations can be obtained.

The fluctuating intensity of the light that is scattered to the detector, i.e. the signal, can be written as $$P(\omega) = i_0^2 \delta(\omega) + \frac{C i_0}{\pi} + i_0^2 S(\omega), \tag{1}$$

where $i_0$ is the mean detected intensity, $S(\omega)$ is the spectrum, and C is a constant.

The first moment of $S(\omega)$ is the mean Doppler shift, $$\langle \omega \rangle = \int_{-\infty}^{\infty} |\omega| S(\omega) d\omega \Big/ \int_{-\infty}^{\infty} S(\omega) d\omega. \tag{2}$$

The mean Doppler shift is proportional to the rms speed of the moving particles $\sqrt{\langle V^2 \rangle}$ as $$\langle \omega \rangle = F(\langle V^2 \rangle^{1/2}, a, \bar{m}) = \langle V^2 \rangle^{1/2} \times \frac{1}{a} \times \left[ \frac{1}{(12\xi)^{1/2}} \beta f(\bar{m}) \right] \tag{3}$$

where V is the velocity of the moving RBC, a represents the size of the scatter (i.e. the radius of spherical scatter or radius of RBC disc), $\xi$ is an empirical factor which is related to the shape of the cells, $\beta=0.17$ is a constant, $\bar{m}$ is the mean number of scattering of photon with RBC, and f ($\bar{m}$) is a function of $\bar{m}$ only. f($\bar{m}$) can be expressed as follows $$f(\bar{m}) = \frac{2}{\pi^{1/2}}\exp(-2\bar{m})\sum_{j=1}^{\infty}\frac{(2\bar{m})^j\Gamma(j+1/2)}{\Gamma(j+1)\Gamma(j)} \propto \begin{cases} \bar{m} & \text{if } \bar{m} \leq 1 \\ (\bar{m})^{1/2} & \text{if } \bar{m} \geq 2m \end{cases} \quad (4)$$

It is noted that the typical values of the quantities in Eq. (3) are as follows: V~0.2-2.0 mm/sec, a<0.15 μm, $\bar{m}$~1.2, ξ~0.1 and β=0.17.

The mean number $\bar{m}$ of scattering of photon with RBC in (3) should be proportional to the total hemoglobin concentration. Replacing $\bar{m}$ by Hgb, we have $$\langle V^2 \rangle^{1/2} \propto \langle \omega \rangle \times \begin{cases} Hgb & \text{if } Hgb \text{ small} \\ Hgb^{1/2} & \text{if } Hgb \text{ large} \end{cases} \quad (5)$$

By using the above equations as a guide for calibration, the blood flow can be calculated. The pulse can also be derived from Doppler blood flow measurements. Some general discussions of Doppler flowmetry and estimating blood flow can be found in P. Elter et al., "Noninvasive, real time laser Doppler flowmetry in perfusion regions and larger vessels", SPIE Proceeding Vol. 3570, pages 244-54, Stockholm, Sweden, 1998; R. Bonner et al., "Model for laser Doppler measurements of blood flow in tissue", Applied Optics, Vol. 20, No. 12, 1981. These publications are incorporated by reference in this application.

The blood flow may also be calculated using laser Doppler flowmetry (LDF). The flow curve obtained may be noisy, and a smooth filtering may be applied to the flow curve before calculating a pulse rate from the flow curve. The Savitzky-Golay (S-G) smoothing filter in time domain may be applied to the data obtained in the flow curve. The S-G filter is described in Savitzky and Golay, *Analytical Chemistry*, Vol. 36, pp. 1627-39 (1964), which is incorporated by reference in this application.

The S-G filter is applied to a series of equally spaced data values $f_i = f(t_i)$, where $t_i = t_o + i\Delta$, for some constant sample time spacing $\Delta$ and i= ... −2, −1, 0, 1, 2, .... The S-G filter replaces each $f_i$ by a linear combination $g_i$ of itself and some number of nearby neighbors, $$g_i = \sum_{n=-n_L}^{n_R} c_n f_{i+n} \quad (6)$$

In equation (6), $n_L$ is the number of points used "to the left" of a data point i (i.e., earlier than it), while $n_R$ is the number used to the right (i.e., later). The S-G filter approximates the underlying function within the moving window by a polynomial, typically quadratic (the $1^{st}$ order) or quartic (the $2^{nd}$ order). For each point $f_i$, it least-squares fits a polynomial to all $n_L + n_R + 1$ points in the moving window, and then set $g_i$ to be the value of that polynomial at point i. The 0-th order S-G filter is also called moving window averaging, which, by letting $g_i$ in equation (6) be a linear combination of $f_i$ s with equal weight, i.e., setting $c_n = 1/(n_L + n_R + 1)$.

The pulse rate can be calculated from the flow curve in time domain by using the following steps. The S-G filter is used to smooth the blood flow curve (i.e., a graph of sample time points on X-axis and blood flow in arbitrary units on the Y-axis), resulting in a secondary smoothed flow curve. In an implementation, this S-G filter may be of 0-th order and with $n_R=0$. In some other embodiments, a higher-order S-G filter may be used.

Then the time difference between any two adjacent peaks of the smoothed flow curve is determined. This time difference is the pulse duration. The pulse duration may then be converted into a pulse rate. Finally, the average pulse rate can be calculated among given number of pulse rates. The average pulse rate can then be used to determine whether the bone is healthy or unhealthy.

A suitable sampling rate can be selected to measure various parameters of the tissue. For monitoring multiple parameters (including oxygen saturation level, hemoglobin concentration, signal level of returned light, blood flow and pulse rate), the system or console may include an analog-to-digital converter 425 for fast data sampling desired for blood flow measurement. For measuring blood flow and pulse, at least one of the radiation sources is continuously on while one of the detectors collects signals at a fast sampling rate. For example, a sampling rate of about two kilohertz (i.e., one sampling per half second) may be used to determine oxygen saturation level or hemoglobin concentration of bone. On the other hand, a sampling of about 100 kilohertz (i.e., one sampling per 0.01 millisecond) may be used to determine the blood flow and pulse rate of bone.

As an illustration, to obtain an oxygen saturation level and a total hemoglobin concentration, a software in the console may send an "X" command to collect oximeter raw data (e.g., intensity of returned light at all the detectors after each of the source emitted) by sampling, for example, once each 10 seconds. In addition, the software may send multiple "C" commands. The "C" commands may send additional 150 emissions via laser diode S1 (at 830 nanometers once every 0.07 seconds) between two successive X commands to measure the blood flow and pulse. The signals from additional laser Doppler flowmetry emissions received by one of the photodiodes (e.g., detector structure D2) may be, with a much higher rate (e.g., 25 kilohertz), transferred to digital information and may be recorded in a separate data file for further analysis. These sampling rates are exemplary, and other suitable sampling rates may be used to collect data.

Any one or combinations of parameters described above can be combined to formulate an overall indicator or index for the health of the bone. In one implementation, the signal level of returned light and blood flow parameters may be combined to formulate an indicator for bone health. In another implementation, the signal level of returned light, total hemoglobin concentration, and blood flow parameters may be combined to formulate an indicator for bone health. In yet another implementation, total hemoglobin concentration, blood flow, and pulse parameters may be combined to formulate an indicator for bone health. In yet another implementation, all five parameters (i.e., the signal level of returned light, total hemoglobin concentration, oxygen saturation level, blood flow, and pulse) may be combined to formulate an indicator for bone health.

Figure 5:
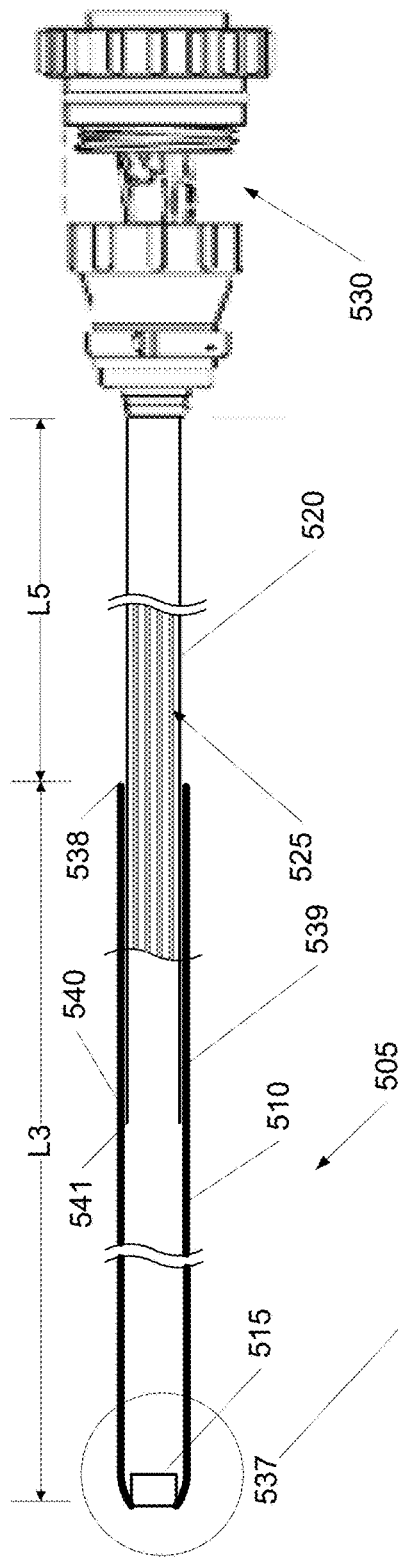
FIG. 5 shows a side view of a bone oximeter probe.
Figure 6:
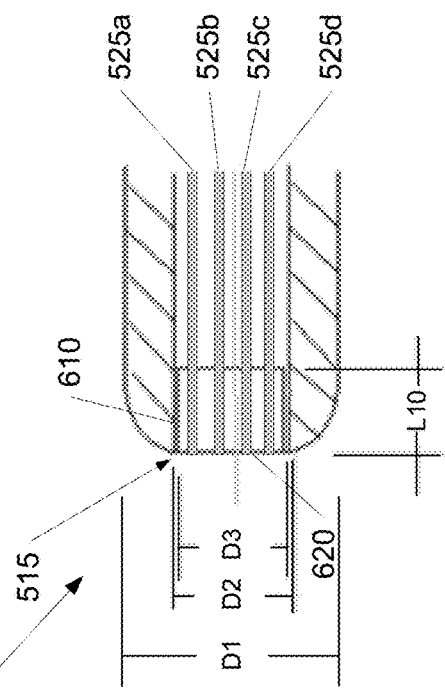
FIG. 6 shows a longitudinal cross-sectional view of the tip of the bone oximeter probe shown in FIG. 5 having optical fibers, forming a forward looking sensor array.

FIG. 5 shows a specific implementation of a bone oximeter probe 505. FIG. 6 shows a longitudinal cross section of a tip of the bone oximeter probe shown in FIG. 5. Bone oximeter probe 505 includes an elongated member 510, a sensor unit 515 at the tip of the elongated member, and a cable 520 extending from the elongated member to a connector 530. In FIG. 5, a portion of the probe is shown cutaway to show optical fibers 525 which extend through a passageway or lumen in the probe.

In a specific implementation, an algorithm to make bone oximeter measurements uses a probe with four optical fibers.

That is, each of the four optical fibers extend from the connector, through the cable, through the elongated member, and to the sensor unit. The ends of the fibers are exposed on a surface of the sensor unit. In this specific implementation, two of the four optical fibers are source fibers while the other two optical fibers are detector fibers. This configuration of the four fibers may be referred to as a 2s2d configuration (i.e., 2 source fibers and 2 detector fibers). This allows for one 2-source and 2-detector pair for making measurements using the algorithm.

In another specific implementation, an algorithm to make bone oximeter measurements uses a probe with six optical fibers. Similar to the 2s2d configuration, each of the six optical fibers extend from the connector, through the cable, through the elongated member, and to the sensor unit where ends of the fibers are exposed on the surface of the sensor unit. In this specific implementation, two of the six optical fibers are source fibers while the remaining four optical fibers are detector fibers. This configuration of the six fibers may be referred to as a 2s4d configuration (i.e., 2 source fibers and 4 detector fibers). This allows for six 2-source and 2-detector pairs for making measurements using the algorithm. For example, if the two sources are identified as S1 and S2, and the four detectors are identified as D1, D2, D3, and D4, a first pair is S1/S2 and D1/D2. A second pair is S1/S2 and D1/D3. A third pair is S1/S2 and D1/D4. A fourth pair is S1/S2 and D2/D3. A fifth pair is S1/S2 and D2/D4. A six pair is S1/S2 and D3/D4.

In this specific implementation of the 2s4d configuration, the algorithm uses a weighted average for the six oxygenation (StO2) values given by each of the six 2-source and 2-detector pairs. So, one benefit of the 2s4d configuration is that a measurement (e.g., an StO2 output) can be made even if one or more of the six 2-source and 2-detector pairs is unable to make a measurement. For example, there may be debris on the sensor head which affects one or more of the six pairs, there may be improper or not good contact with one or more of the six pairs and the bone surface, and so forth.

A benefit of the 2s2d configuration is that it allows for a smaller sensor head (e.g., small sensor head surface) since the sensor head has four fibers instead of six fibers. Small sensor heads are generally desirable because they can be used with small incisions in soft tissue to gain access to the underlying bone. With a small incision, there is typically less cutting of the patient's tissue, less blood loss, less pain, less scaring, less risk of infection, and so forth as compared to a large incision. Thus, depending upon the specific surgical scenario a doctor may select the 2s2d configuration over the 2s4d configuration or vice versa. In making the selection, the doctor may weigh factors such as the depth of the bone within the soft tissue, size of the bone to be measured, the patient's health, and other factors.

In various other implementations, the algorithm can be adapted to use any number of source and detector fibers. Some examples of other source and detector fiber configurations include 1s1d (one source and one detector fiber), 1s2d (one source and two detector fibers), 1s3d (one source and three detector fibers), 2s1d (two source and one detector fiber), 2s3d (two source and three detector fibers), 4s4d (four source and four detector fibers), and so forth. A number of source fibers in a probe may equal a number of detector fibers such as in the 2s2d configuration. A number of source fibers in a probe may be less than a number of detector fibers such as in the 2s4d configuration. A number of source fibers in a probe may be greater than a number of detector fibers.

The sensor unit includes distal ends of the optical fibers. Connector 530 connected to an end of the cable includes proximal ends of the optical fibers. The cable encases the optical fibers in a cable jacket. In FIG. 5, the connector is shown disassociated or exploded to show proximal end portions of the optical fibers. In the embodiment shown in FIG. 5, the optical fibers run continuously from the sensor unit to the connector. However, in other embodiments, the optical fibers may be interrupted by, for example, an amplifier, beam combiner, or other device between the sensor unit and connector.

Typically, the elongated member will be made to be rigid or made of a rigid material. This allows the user to hold the elongated member with the sensor head against the bone without having the elongated member collapse. In a specific implementation, elongated member 510 is a hollow metal tube, such as an aluminum tube. However, the elongated member can be made of any material (e.g., plastic). In this specific implementation, the tube has a circular cross section. However, the cross section can have any shape (e.g., square, rectangle, oval, or ellipse).

Lengths L3 and L5 indicate lengths of the elongated member and cable, respectively. In a specific implementation, length L5 is greater than length L3. However, length L5 may be less than or equal to length L3. To use the probe, the surgeon (or a robot) holds the elongated member. The elongated member thus has a length that permits it to be held such as by the hand of the surgeon. In a specific implementation, length L3 is about 200 millimeters and length L5 is about 3000 millimeters. But, length L3 can range from about 100 millimeters to about 500 millimeters. This includes, for example, 125, 150, 175, 225, 250, 275, 300, 325, 350, 375, 400, 425, 450, 475, or 499 millimeters. Length L3 may be less than 100 millimeters or greater than 500 millimeters.

Figure 28:
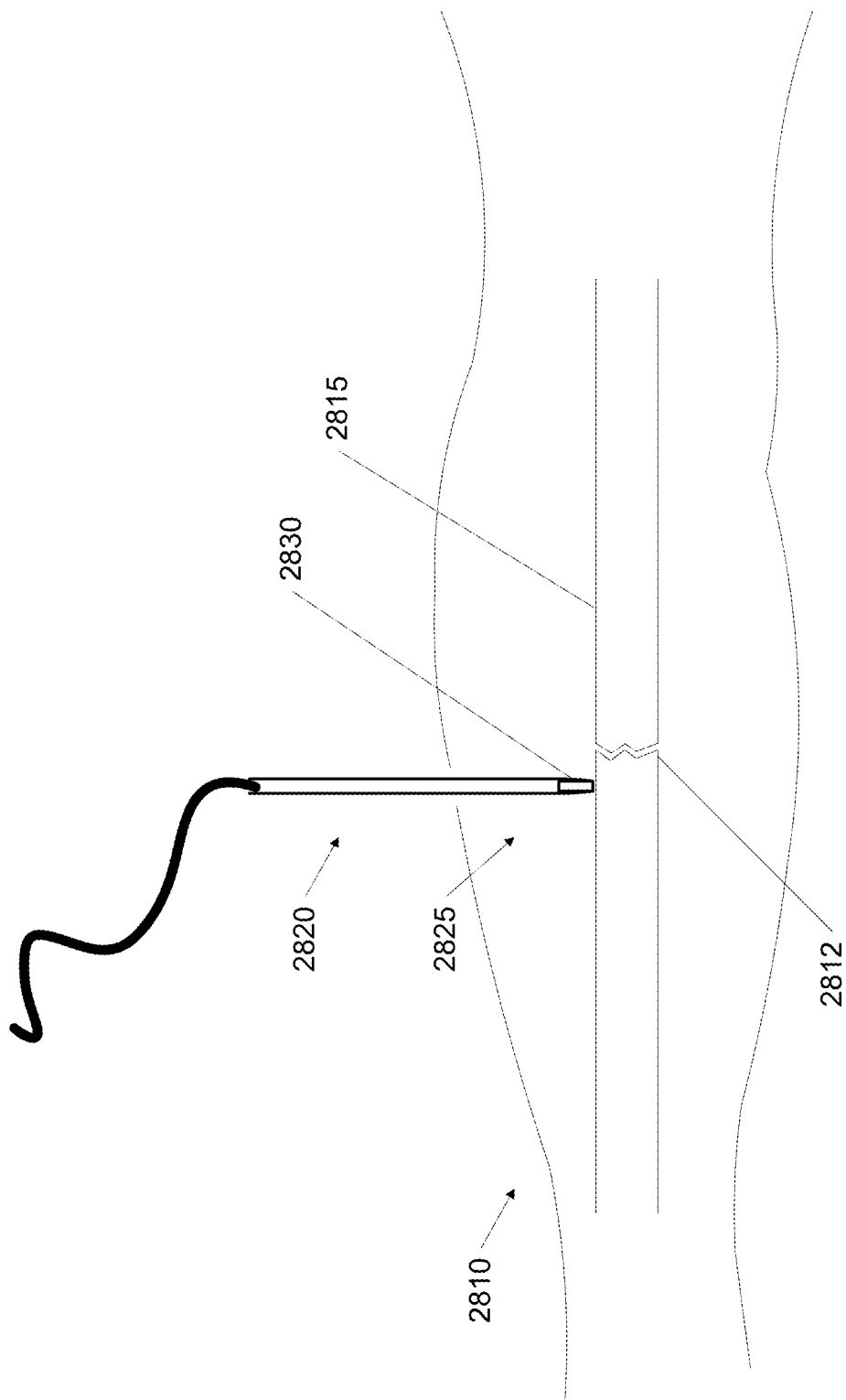
FIG. 28 shows a pictorial diagram of a bone oximeter probe being advanced into soft tissue to obtain a measurement of the underlying bone.

A probe having a long elongated member can be inserted further into soft tissue to reach the underlying bone as compared to a probe having a short elongated member (FIG. 28). However, if the elongated member is too long, it may be difficult and awkward to position and manipulate the probe. Thus, selecting an elongated member having the desired length can depend on factors such as the distance between the target location on the bone to be measured and the location of the incision in the soft tissue for the probe to be inserted.

In a specific implementation, length L3 of the elongated member is fixed. That is, the length is not adjustable by the user. In another implementation, length L3 is adjustable. In this specific implementation, the elongated member includes a series of telescoping sections with each section having a progressively smaller width or diameter. To lengthen the elongated member, the user holds a first telescoping section and pulls a second telescoping section away from the first telescoping section. This allows the second telescoping section to extend away from the first telescoping section. To shorten the elongated member, the user holds the first telescoping section and pushes the second telescoping section towards the first telescoping section. This collapses the second telescoping section into the first telescoping section.

In another implementation, the length of the elongated member is adjusted by connecting or disconnecting one or more sections of the elongated member. In this specific implementation, the elongated member includes a set of connectable sections. To lengthen the elongated member, the user can connect two or more sections of the elongated member together (e.g., push together and twist). To shorten the elongated member, the user can disconnect and remove one or more sections (e.g., untwist and pull).

In a specific implementation, the elongated member is straight. That is, the elongated member does not have any bends, angles, curves, or changes in direction.

In another implementation, the elongated member is not straight. For example, the elongated member may have one or more angles or bends to help the surgeon position the probe against the bone to be measured. In this specific implementation, the elongated member includes a joint that connects a first section to a second section of the elongated member. An angle is between the first and second section In a specific implementation, the angle or joint is fixed and can not be adjusted by the user. An angle between two sections of the elongated member may be about 30, 40, 45, 60, or 90 degrees. The angle can range from about 90 degrees to about 179 degrees. The angle can be less than 90 degrees or more than 179 degrees.

In another implementation, the angle or joint is adjustable. In this specific implementation, the user can hold the first section and move or pivot the second section relative to the first section to adjust the angle between the first and second sections. The joint between the two sections may be lockable so that the first and second sections do not accidentally move.

The joint can be made to have any number of degrees of freedom. The joint may be a hinge so that the sections can move up and down, but not left and right. The joint may be a ball and socket mechanism where one of the first or second sections includes the ball and another of the first or second sections include the socket. This allows, for example, the first section to move, relative to the second section, up and down, and left and right.

In another specific implementation, the elongated member or a portion of the elongated member is bendable. For example, the elongated member may be implemented as a gooseneck or a flexible jointed metal pipe. The gooseneck can be manually bent or adjusted into any desired configuration so as to avoid interference with, for example, other instruments in the operating area.

Cable 520 will typically be made to be flexible or made of a flexible material. This allows the probe to be routed around various structures or instruments in the surgical area. In a specific implementation, the cable length (i.e., length L5) is about 3000 millimeters. Length L5 can range from about 1000 millimeters to about 6000 millimeters. This includes, for example, 1500, 2000, 2500, 3000, 3500, 4000, 4500, 5000, 5500, or 5999 millimeters. Length L5 may be less than 1000 millimeters or greater than 6000 millimeters.

As shown in FIG. 5, a portion 539 of the cable is inserted into the elongated member (i.e., is inserted into a proximal end 538 of the elongated member). That is, at least a portion 540 of the elongated member overlaps a portion of the cable. In this specific implementation, the cable and elongated member have circular cross sections. An outer diameter of the cable is less than an inner diameter of the elongated member so that the cable can be inserted or fitted into the elongated member.

The cable may be inserted any distance into the elongated member. For example, the cable may be inserted into the elongated member such that an entire length of the elongated member overlaps the cable. That is, the cable extends through the elongated member and to the sensor head. The cable may be partially inserted into the elongated member such that the cable terminates before reaching the sensor head. For example, the cable may be inserted into the elongated member such that it terminates at a midpoint of the length of the elongated member. The cable may be inserted into the elongated member such that it extends into the elongated member for about three-quarters, one-half, one-third, one-quarter, one-eighth, or one-sixteenth of the length of the elongated member.

In a specific implementation, a length of the elongated member is about 200 millimeters. In various implementations, the cable is inserted to a depth of about 150 millimeters within the elongated member, i.e., three-quarters the length of the elongated member. That is, a length of the cable from proximal end 538 of the elongated member to an end 541 of the cable is about 150 millimeters. The cable can extend any depth or distance into the elongated member. The depth can range from about 10 millimeters to about 200 millimeters (i.e., the entire length of the elongated member). This includes, for example, about 12, 20, 25, 30, 40, 50, 60, 67, 70, 80, 90, 100, 110, 120, 130, 140, 160, 170, 180, 190, or 199 millimeters. The depth of insertion may be less than 10 millimeters or greater than 199 millimeters. Generally, the further the cable is inserted into the elongated member, the less likely it is that the cable and elongated member can separate accidentally. For example, there will be a greater amount of surface area for bonding between the elongated member and the cable. However, longer lengths of cable can increase costs. Therefore, the cable is typically inserted into the elongated member to a depth or distance sufficient to prevent accidental separation during normal use.

Securing the cable and elongated member together by inserting the cable into the elongated member can help eliminate the need for another component such as a coupler between the cable and elongated member to secure the cable and elongated member together. Eliminating a component can reduce the cost of the probe.

In other implementations, the elongated member is inserted into the cable and at least a portion of the cable overlaps a portion of the elongated member. The elongated member may inserted into the cable such that the cable overlaps the entire length of the elongated member and the elongated member is not visible. The elongated member may be partially inserted into the cable so that a portion of the elongated member not inserted into the cable is visible.

Any technique may be used to secure the elongated member and cable together. In a specific implementation, an adhesive such as epoxy is used to attach the cable to the elongated member. In this specific implementation, a portion of the cable is coated with a layer of the adhesive. The cable is then inserted into the elongated member and the adhesive dries or cures to secure the cable and elongated member together.

In another specific implementation, friction between the surface of the elongated member (i.e., inner surface) and the surface of the cable (i.e., outer surface) is used to help prevent the elongated member and cable from separating. The elongated member may include threads (i.e., internal or female threads) so that the elongated member can be screwed to twisted onto the cable. As the elongated member is twisted on the threads of the elongated member may cut corresponding threads onto the cable.

In another implementation, one of the elongated member or cable is not inserted into another of the elongated member or cable. Rather, in this specific implementation, the ends of the elongated member and cable are butted together. For example, an end of the elongated member may be glued, welded, taped, or fused to an end of the cable. The end of the elongated member may have a barbed connector so that the end of the cable can be pushed and stretched over the barbed connector. In a specific implementation, a coupling device is used to connect the elongated member and cable together. The coupling device has a first end and a second end, opposite the first end. The first end receives an end of the elongated member and the second end receives an end of the cable.

As shown in FIG. 6, a tip 537 of the bone oximeter probe has sensor unit 515 (sometimes referred to as a sensor head) which includes a block 610 with four channels or holes extending along the longitudinal axis of the block. The distal end portions of optical fibers 525a, 525b, 525c, and 525d are inserted into each channel in the block. An adhesive, such as epoxy, may be used to secure or attach the optical fibers to the channels in the block.

The channels in the block separate and fix distal ends of the optical fibers by a suitable distance to optimize optical measurements for a given bone. There can be any number of channels in the block (e.g., one, two, three, four, five, six, or more than six channels). The block may extend the entire length of the elongated member; alternatively, the block may be present only at the distal end of the probe (or elongated member), as shown in FIG. 6, to firmly fix the distal end portions of the optical fibers.

Any suitable material can be used for the block as long as it is chemically and structurally stable, and does not interfere with transmission of optical signals in the optical fibers. For example, the block can be made of an aluminum alloy (e.g., 6061 aluminum alloy) with channels for threading optical fibers through. Then the aluminum alloy block can be attached to the inner surface of the elongated member at the tip using an adhesive, such as Epotek 353ND epoxy.

The block can be attached to the elongated member using other attachment mechanisms instead of or in addition to an adhesive. For example, the block and elongated member may have threads so that the block can be screwed into the elongated member. The block may be attached to the elongated member using a press fit or interference fit. The block may be welded or brazed to the elongated member. The block may be integrally formed with the elongated member as a single unit, such as via injection molding using a single mold to form the elongated member and block.

Although FIGS. 5 and 6 show the block inserted into the elongated member or inside the elongated member, the block or a portion of the block may be outside the elongated member. For example, the block may be a cap which fits over the tip of the elongated member. The cap can have channels for holding the fiber optic cables.

FIG. 6 shows some dimensions of the probe tip. In a specific implementation, the block and elongated member are cylindrical in shape. That is, cross sections of the block and elongated member have the shape of a circle. Diameters D1 and D2 indicate outer and inner diameters, respectively, of the elongated member. A diameter D3 indicates a diameter of the block. A length L10 indicates a length of the block.

In this specific implementation, diameter D1 is about 7 millimeters, but can range from about 4 millimeters to about 14 millimeters. This includes, for example, 4.5, 5, 5.5, 6, 6.5, 7.5, 8, 8.5, 9, 9.5, 10, 10.5, 11, 11.5, 12, 12.5, 13, 13.5, or 13.9 millimeters. Diameter D1 may be less than 4 millimeters or greater than 14 millimeters.

In a specific implementation, diameter D2 is about 6 millimeters, but can range from about 3 millimeters to about 12 millimeters. This includes, for example, 3.5, 4.5, 5, 5.5, 6, 6.5, 7, 7.5, 8, 8.5, 9, 9.5, 10, 10.5, 11, 11.5, or 11.9 millimeters. Diameter D2 may be less than 3 millimeters or greater than 12 millimeters.

In a specific implementation, diameter D3 is about 5.5 millimeters, but can range from about 2 millimeters to about 10 millimeters. This includes, for example, 2.5, 3, 3.5, 4, 4.5, 5, 5.5, 6, 6.5, 7, 7.5, 8, 8.5, 9, 9.5, or 9.9 millimeters. Diameter D3 may be less than 2.5 millimeters or greater than 10 millimeters.

In a specific implementation, length L10 of the block is about 5 millimeters, but can range from about 2 millimeters to about 10 millimeters. This includes, for example, 2.5, 3, 3.5, 4, 4.5, 5, 5.5, 6, 6.5, 7, 7.5, 8, 8.5, 9, 9.5, or 9.9 millimeters. Length L10 may be less than 2 millimeters or greater than 10 millimeters.

The block has a surface or face 620 which faces the bone to be measured. In a specific implementation, an area of the face is about 23.8 square millimeters. An area of the face may be about 24 square millimeters or less, but can range from about 5 square millimeters to about 80 square millimeters. This includes, for example, 10, 15, 20, 25, 30, 35, 40, 45, 50, 55, 60, 65, 70, 75, or 79.9 square millimeters. The area may be less than 5 square millimeters or greater than 80 square millimeters. Sensor heads having small faces (i.e., small surface areas) may be used where only a small portion of the surface of the bone is exposed or available. Small sensor heads are desirable because they allow for smaller incisions in the soft tissue to reach the underlying bone as compared to large sensor heads.

It should be appreciated that these dimensions and other dimensions discussed in this application may vary widely depending upon the application, the dimensions of the bone to be measured, or both. Generally, it will be desirable to select a sensor head with a sensor surface that can make good contact (e.g., full contact) with the surface of the bone to be measured. This helps to ensure that light from the sensor head is directed into the bone and that reflected light from the bone (not ambient light) is received at the sensor head.

In a specific implementation, the face of the block has a dull finish. This can help to ensure that that more of the light which is transmitted into the bone is received back at the detectors, instead of being reflected off the face. The face of the block may be processed (e.g., polishing, sanding, bluing, anodizing, or oxidizing) to make the face more dull than the original starting material. In a specific implementation, the face is processed with a final polish of a 5 micron grit abrasive for a dull finish on the face. The abrasive may be a piece of paper (e.g., sandpaper), a polishing compound, or a stone. The face may be colored (e.g., black flat color), finished (e.g., matte finish), textured (e.g., bead-blasted finish), or combinations of these, to reduce reflectivity.

It should be appreciated that the block, elongated member or both may not necessarily have a cylindrical shape. In various implementations, the block, elongated member or both have a rectangular shape and dimensions are with respect to widths and lengths. The block, elongated member or both have a triangular shape and dimensions are with respect to bases and altitudes or heights. The block, elongated member or both have an elliptical or oval shape and dimensions are with respect to a major axis (or transverse diameter) and a minor axis (or conjugate diameter). It should be appreciated that the block, elongated member or both can have any cross-sectional shape.

This specific implementation of the bone oximeter probe may be referred to as a probe with a forward-looking sensor array. In this specific implementation, the sensor head (or sensor head surface) is positioned with respect to the elongated member such that the optical fibers extend through the probe or through the elongated member and to the sensor head surface without changing direction. The optical fibers are straight (i.e., not bent). In other words, the sensor head surface is positioned with respect to the elongated member such that an axis passing through the elongated member passes through the sensor head surface. When holding or pointing the elongated member towards the bone to be measured, the sensor head surface will be facing the bone. Thus, the doctor will not have to reorient the probe to make the sensor head face the bone which can be difficult when the sensor head is within an incision. In other implementations, a bone oximeter probe may instead or additionally have a side-looking sensor array such as shown in FIGS. 15-17 and discussed below.

FIGS. 7-12 show various specific implementations of arrangements for sensor structures or openings of a probe. Any of these implementations may be used in conjunction with any of the implementations discussed in this application. The sensor structures can be either source structures or detector structures. Although specific numbers of sensor structures are shown, the arrangements can be expanded or reduced to have more sensor structures per column, more sensor structures per row, less sensor structures per column, less sensor structures per row, or combinations of these.

Figure 7:
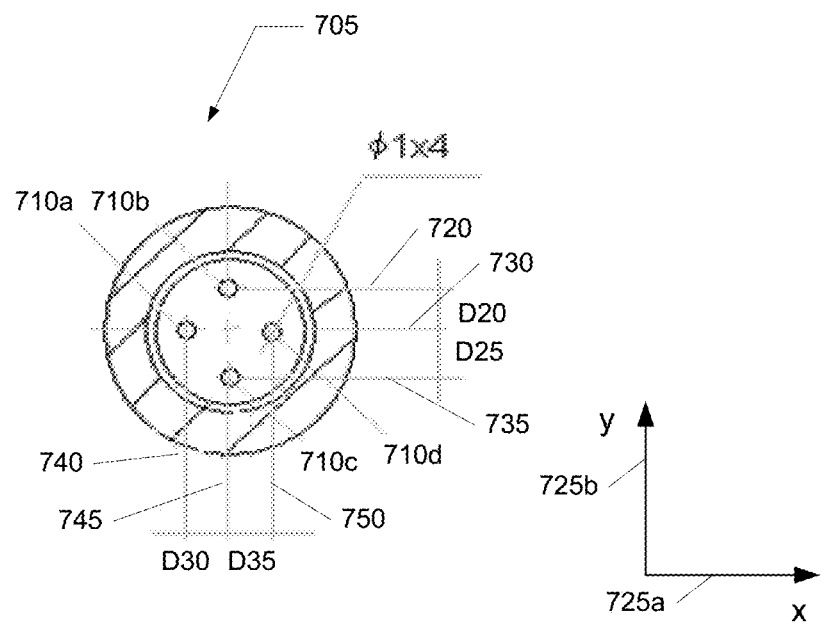
FIG. 7 shows a front view of a tip of an oximeter probe having a first sensor arrangement.

FIG. 7 shows a front view of a probe 705. This probe has four structures 710*a-d*. Structure 710*a* is in a first column. Structures 710*b-c* are in a second column. Structure 710*d* is in a third column. Each column has three rows. Structure 710*b* is in a first row. Structures 710*a* and 710*d* are in a second row. Structure 710*c* is in a third row. In other implementations, there can be any number of structures arranged in any number of desired rows and columns (e.g., one by two, one by three, one by four, two by two, or two by four).

This application describes the arrangement of sensors as an array of rows and columns, but as one of skill in the art will recognize, the entire array can be rotated ninety degrees, so that rows become columns and columns become rows. A row may have a different number of structures than another row. A column may have a different number of structures than another column. A row or column may be composed entirely of one type of structure, either source or detector. A row or column may be composed of both source and detector.

In a first arrangement, structures 710*a-b* are source structures (i.e., first and second source structures, respectively) and structures 710*c-d* are detector structures (i.e., first and second detector structures). In other implementations, any of the structures can be assigned as sources or detectors as desired.

The intensity of light emitted by the source structures may be the same or the intensity may vary. For example, in a specific implementation of the first arrangement, first source structure 710*a* emits light at an intensity that is the same as second source structure 710*b*. In another implementation, first source structure 710*a* emits light at an intensity that is different from second source structure 710*b*. For example, the intensity of light emitted by second source structure 710*b* may be greater than the intensity of light emitted by first source structure 710*a*. This can help to compensate for the attenuation of light if a distance between second source structure 710*b* and first detector structure 710*c* is greater than a distance between first source structure 710*a* and second detector structure 710*d*.

In FIG. 7, the structures shown are circular. However, in other implementations, the structures can have any shape, such as square, rectangle, hexagon, octagon, ellipse, any polygon shape, or any quadrilateral shape. In a specific implementation, each structure has the same cross-sectional area (e.g., same diameter). In another implementation, the cross-sectional area of one or more structures may be different from other structures. There can be any combination of differently sized structures.

In this specific implementation, each structure has a diameter of about 1 millimeter. More specifically, each structure includes an optical fiber bundle having a diameter of about 1 millimeter. The optical fiber bundle includes borosilicate glass fibers having a diameter of 33 microns or micrometers. The diameter of a structure or optical fiber bundle can range from about 0.5 millimeters to about 2 millimeters. This includes, for example, 0.6, 0.7, 0.8, 0.9, 1.1, 1.2, 1.3, 1.4, 1.5, 1.6, 1.7, 1.8, or 1.9 millimeters. The diameter may be less than 0.5 millimeters or greater than 2 millimeters. Smaller diameter structures may be desirable for smaller bones. This helps to ensure that gaps between the structure and the surface of the bone is minimized so that light from a source structure does not escape through a gap and ambient light does not enter through the gap and be detected by the detector structure.

Using optical fiber instead of photodetectors and emitters (e.g., light emitting diodes) can reduce the cost of the probe because, typically, optical fiber is less expensive than photodetectors and diodes. Further, the probe face can be made to have a small surface area which can be desirable because such a probe face will not need a large surface area of bone to be exposed.

In other implementations, wires or cables may be connected to the structures. One or more of the structures may include a photodiode or other emitter device, a photodetector or other detector device, or fiber optic cable, in any combination.

Distances between columns and rows can be the same or different. Distance can be measured from a reference line for each column and row where the reference line passes through a reference point of the structure. For example, this reference point may be the centers of the structures.

Thus, in FIG. 7, a first reference line 720, parallel to an x-axis 725*a*, passes through a reference point of second source structure 710*b*. A second reference line 730, parallel to the x-axis, passes through reference points of first source structure 710*a* and second detector structure 710*d*. A third reference line 735, parallel to the x-axis, passes through a reference point of first detector structure 710*c*. A fourth reference line 740, parallel to a y-axis 725*b*, passes through first source structure 710*a*. A fifth reference line 745, parallel to the y-axis, passes through second source structure 710*b* and first detector structure 710*c*. A sixth reference line 750 parallel to the y-axis passes through second detector structure 710*d*.

In a specific implementation, the sensor structures are asymmetrically arranged. A distance D20 between the first and second reference lines is different from a distance D25 between the second and third reference lines. Distance D20 may be about 1.5 millimeters, but can range from about 0.5 millimeters to about 3 millimeters. This includes, for example, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, or 2.9 millimeters. Distance D20 may be less than 0.5 millimeters or greater than 3 millimeters.

Distance D25 may be about 2 millimeters, but can range from about 1 millimeter to about 4 millimeters. This includes, for example, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, or 3.9 millimeters. Distance D25 may be less than 1 millimeter or greater than 4 millimeters.

In another implementation, the sensor structures are symmetrically arranged. Distances D20 and D25 are the same. For example, distances D20 and D25 may be about 1.5 millimeters. A sensor head having a symmetrical arrangement of sensor structures can accommodate a desire to have a small sensor head (i.e., a sensor head having a small surface area) and a desire to have a large source and detector separation. When using a small sensor head, there is typically less bone that will be exposed as compared to using a large sensor head. A large source and detector separation allows measurements to be made deeper into the bone as compared to a small source and detector separation. To achieve a large source and detector separation with a sensor head having a symmetrical shape or surface (e.g., circle), the source structures can be placed close to an edge of the sensor head surface while the detector structures are placed to close to opposite or diametric edges of the sensor head surface. In this specific implementation, this creates a symmetrical arrangement of sensor structures when the structures are so arranged.

A distance D30 between the fourth and fifth reference lines is the same as a distance D35 between the fifth and sixth reference lines. Distances D30 and D35 may be about 1.5 millimeters, but can range from about 0.5 millimeters to about 3 millimeters. This includes, for example, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, or 2.9 millimeters. Distances D30 and D35 may be less than 0.5 millimeters or greater than 3 millimeters. In another implementation, distance D30 may be different from distance D35.

The sensor arrangement shown in FIG. 7 may be referred to as a kite or deltoid array of sensors. A deltoid is a quadrilateral with two disjoint pairs of congruent sides. In this specific implementation, structures 710a-d form the vertices of a deltoid. A first side of the deltoid is between first and second source structures 710a-b. A second side of the deltoid is between second source structure 710b and second detector structure 710d. A third side of the deltoid is between first and second detector structures 710c-d. A fourth side of the deltoid is between first source structure 710a and first detector structure 710c.

Lengths of the first and second sides of the deltoid are the same. Lengths of the third and fourth sides of the deltoid are the same. A length of the first or second side is less then a length of the third or fourth side. The first side is not parallel with the second, third, or fourth sides. The second side is not parallel with the third and fourth sides. The third side is not parallel with the fourth side. A first diagonal is from second source structure 710b to first detector structure 710c. A second diagonal is from first source structure 710a to second detector structure 710d. The first diagonal bisects the second diagonal at right angles.

In another implementation, the sensors are arranged in a symmetrical diamond or square array. In other words, structures 710a-d form the vertices of a square. A first side of the square is between first and second source structures 710a-b. A second side of the square is between second source structure 710b and second detector structure 710d. A third side of the square is between first and second detector structures 710c-d. A fourth side of the square is between first source structure 710a and first detector structure 710c. The first side is perpendicular to the second and fourth sides. The second side perpendicular to the first and third sides. The third side perpendicular with the second and fourth sides. The first side is parallel with the third side. The second side is parallel with the fourth side.

Lengths of the first, second, third, and fourth sides of the square are the same. In this specific implementation, distances D20, D25, D30, and D35 are equal. For example, distances D20, D25, D30, and D35 may be about 1.5 millimeters.

Structures 710a-d may be arranged to form the vertices of any shape. Some examples of shapes include a polygon, convex polygon, non-convex polygon, equiangular polygon, cyclic, equilateral, isotoxal, regular, rectilinear, quadrilateral, convex quadrilateral, concave quadrilateral, rectangle, parallelogram, rhombus, rhomboid, kite, deltoid, tangential quadrilateral, and trapezium.

In a specific implementation, a first distance extends between the first source structure and the first detector structure without touching another source or detector structure. A second distance extends between the second source structure and the second detector structure without touching another source or detector structure. The first distance is different from the second distance.

Figure 8:
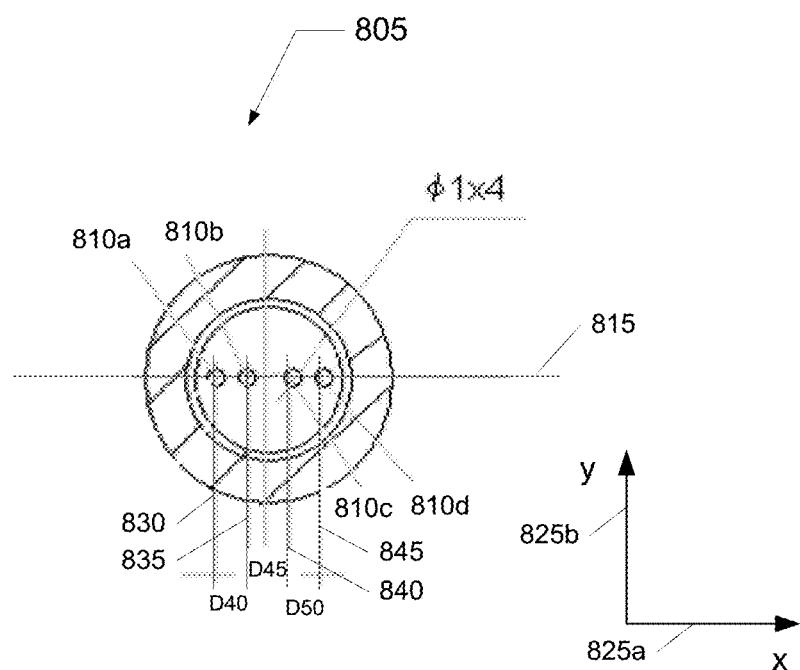
FIG. 8 shows a front view of a tip of an oximeter probe having a second sensor arrangement.

FIG. 8 shows a front view of a specific implementation of a probe 805. In this probe, structures 810a-d are arranged symmetrically in one row and four columns. Structures 810a-b are source structures (i.e., first and second source structures, respectively) and structures 810c-d are detector structures (i.e., first and second detector structures, respectively). This arrangement of structures may be referred to as a linear arrangement. This sensor head may be referred to as a linear two-source two-detector sensor (i.e., linear 2s2d sensor). Distances between adjacent structures may be equal or different.

For example, a first reference line 815, parallel to an x-axis 825a, passes through reference points of structures 810a-d. A second reference line 830, parallel to a y-axis 825b, passes through a reference point of first source structure 810a. A third reference line 835, parallel the y-axis, passes through a reference point of second source structure 810b. A fourth reference line 840, parallel to the y-axis, passes through a reference point of first detector structure 810c. A fifth reference line 845, parallel to the y-axis, passes through a reference point of second detector structure 810d.

A first distance D40 is between the second and third reference lines. A second distance D45 is between the third and fourth reference lines. A third distance D50 is between the fourth and fifth reference lines.

In a specific implementation, the first, second, and third distances are the same. The first, second, and third distances may be about 1.5 millimeters. In another implementation, at least one distance is different from another distance. For example, the first distance may be different from the second and third distances. The second distance may be different from the third distance.

In a specific implementation, the first reference line is coincident with a diameter or diagonal of the sensor head face. An axis passing through the elongated member that is connected to the sensor head is perpendicular to the first reference line. In another implementation, sensor structures are not aligned with the diameter of the sensor head face. The sensor structures may be aligned with a chord of the sensor head face.

Selection of a sensor head having a specific arrangement of sensors may depend on the type of bone to be measured. For example, the linear array of sensors (FIG. 8) may be more desirable for bones that are small and long as compared to bones that are wide and flat because the linear array of sensors can be aligned with the axis of the bone. The sensor head of FIG. 8 may make better contact with the small and long bone as compared to the sensor head of FIG. 7. Conversely, the rectangular or deltoid array of sensors (FIG. 7) may be more desirable for bones that are wide and flat as compared to bones that are small and long.

The length and width of the source and detector array may be customized for certain types of bone to better match the anatomy. In a specific implementation, a probe includes pluggable sensor heads. A user can unplug a sensor head of a first type (e.g., linear sensor array) from a probe and plug a sensor head of a second type (e.g., rectangular sensor array) into the probe.

Figure 9:
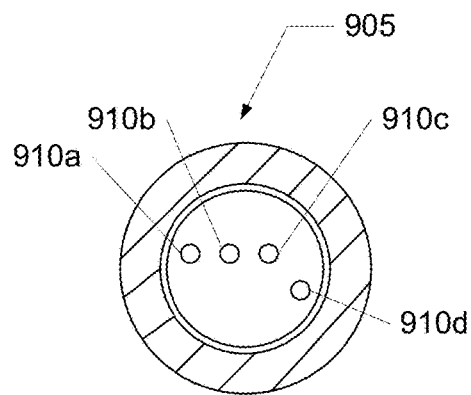
FIG. 9 shows a front view of a tip of an oximeter probe having a third sensor arrangement.

FIG. 9 shows a front view of a specific implementation of a probe 905. In this probe, structures 910a-d are arranged asymmetrically in two rows and four columns. Structures 910a-b are source structures (i.e., first and second source structures, respectively) and structures 910c-d are detector structures (i.e., first and second detector structures, respectively). First and second source structures and the first detector structure are aligned linearly. The second detector structure is offset from the rest of the sensor structures and is not aligned linearly with the first and second source structures and the first detector structure.

In other words, a first row includes first and second source structures and the first detector structure. A second row includes the second detector structure. First, second, third, and fourth columns include the first source structure, second source structure, first detector structure, and second detector structure, respectively.

A first reference line, parallel to an x-axis, passes through the first and second source and first detector structure. A second reference line, parallel to the x-axis, passes through the second detector structure. The first and second reference lines are not coincident. In other words, second reference line is offset from the first reference line. The second reference line may be offset from the first reference line by any distance (e.g., 0.5, 1, 1.5, 2, 2.5, or 3 millimeters).

A third reference line, parallel to a y-axis, passes through the first source structure. A fourth reference line, parallel to the y-axis, passes through the second source structure. A fifth reference line, parallel to the y-axis passes through the first detector structure. A sixth reference line, parallel to the y-axis, passes through the second detector structure.

A first distance is between the third and fourth reference lines. A second distance is between the fourth and fifth reference lines. A third distance is between the fifth and six reference lines.

In a specific implementation, the first, second, and third distances are the same. In another implementation, at least one distance is different from another distance. For example, the first distance may be different from the second and third distances. The second distance may be different from the third distance.

Figure 10:
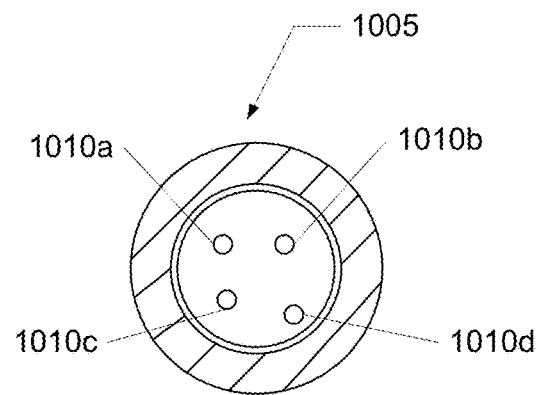
FIG. 10 shows a front view of a tip of an oximeter probe having a fourth sensor arrangement.

FIG. 10 shows a front view of a specific implementation of a probe 1005. In this probe, structures 1010a-d are arranged asymmetrically in two rows and two columns. Structures 1010a-b are source structures (i.e., first and second source structures) and structures 1010c-d are detector structures (i.e., first and second detector structures). First and second source structures and the first detector structure are equidistant from the center of the probe face. The second detector structure is farther away from the center of the probe face compared to the other three structures. Also, a line drawn through the first and second source structures is not parallel to a line drawn through the first and second detector structures.

In other words, a first row includes first and second source structures. A second row includes first and second detector structures. However, the second detector structure is offset from the first detector structure in a vertical direction or in a direction parallel to the y-axis.

A first column includes the first source and first detector structures. A second column includes the second source and second detector structures. However, the second detector structure is offset from the second source structure in a horizontal direction or in a direction parallel to the x-axis. A structure may be offset with respect to both horizontal and vertical directions, offset with respect to the horizontal direction only, or offset with respect to the vertical direction only.

Figure 11:
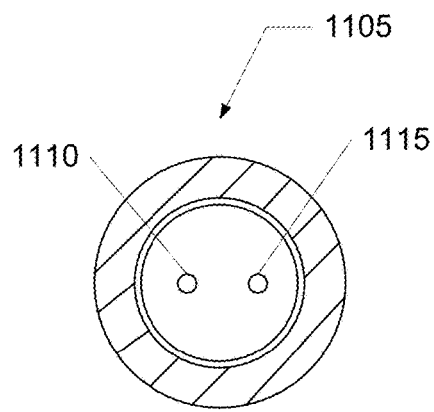
FIG. 11 shows a front view of a tip of an oximeter probe having a fifth sensor arrangement.

FIG. 11 shows a front view of a specific implementation of a probe 1105. This probe has one source structure 1110 and one detector structure 1115. This sensor head may be referred to as a linear one-source one-detector sensor (e.g., a linear 1sld sensor). A distance between a center of the probe face and the source structure may be equal to or different from a distance between the center of the probe face and the detector structure.

Figure 12:
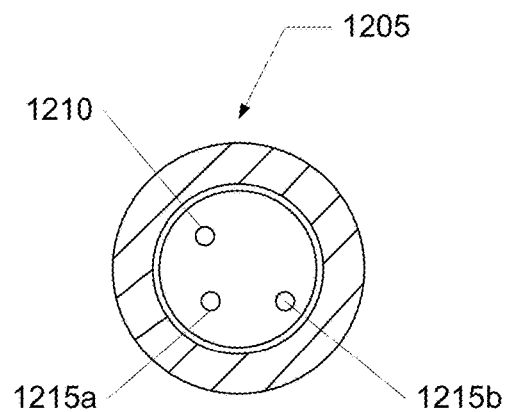
FIG. 12 shows a front view of a tip of an oximeter probe having a sixth sensor arrangement.

FIG. 12 shows a front view of a specific implementation of a probe 1205. This probe has one source structure 1210 and two detector structures 1215a-b (i.e., first and second detector structures). A distance between the source structure and the first detector structure may be equal to or different from a distance between the source structure and the second detector structure.

The source structure and first and second detector structures may be arranged to form the vertices of a triangle. A first side of the triangle is between the source structure and first detector structure. A second side of the triangle is between the first and second detector structures. A third side of the triangle is between the source structure and the second detector structure.

In a specific implementation, the triangle is a right triangle such that the third side forms the hypotenuse and the first and second sides are perpendicular to each other. A length of the third side is greater than lengths of the first and second sides. The structures may be arranged to form other types of triangles such as an isosceles, scalene, equilateral, oblique, acute, or obtuse triangle.

Generally, a source structure and a detector structure are separated by a larger distance when optical measurements from a deeper volume of bone are desired. Thus, a sensor unit with a larger distance between a source structure and a detector structure can generally measure optical parameters deeper into the tissue. In other words, the distance between the source and detector (i.e., "source-detector separation") can indicate the approximate depth below the surface of the bone at which a measurement will be made.

More specifically, if the source-detector separation of the sensor is "S" then the region of bone below the surface of the bone (or below the sensor) that will be measured will have a cubic volume of S×S×S (S by S by S). For example, if a sensor has a source-detector separation that is 5 millimeters, the region measured below the surface of the bone has a cubic volume of about 5 millimeters by 5 millimeters by 5 millimeters. As another example, if a sensor has a source-detector separation that is 2.2 millimeters, the region measured below the surface of the bone has a cubic volume of about 2.2 millimeters by 2.2 millimeters by 2.2 millimeters. Thus, typically, the source-detector separation will not be greater than a thickness of the bone; otherwise, the sensor may make a measurement of a region outside of the bone.

For example, the human femur bone has a cortical wall that varies in thickness from about 2 millimeters to about 10 millimeters. Thus, to measure the bone oxygenation of a cortical wall that is about 2 millimeters thick, it may be desirable to use a sensor head having a source-detector separation of less than 2 millimeters. To measure the bone oxygenation of a cortical wall that is about 10 millimeters thick, it may be desirable to use a sensor head having a greater source-detector separation so that a deeper region of the cortical wall is measured. In a specific implementation, a measurement depth of a bone oximeter probe is about 5 to about 10 millimeters.

In a specific implementation, a distance between a source and detector structure is about 3.5 millimeters or less, but can range from about 1 millimeter to about 10 millimeters. This includes, for example, 1.5, 2, 2.5, 3, 3.5, 4, 4.5, 5, 5.5, 6, 6.5, 7, 7.5, 8, 8.5, 9, 9.5, or 9.9 millimeters. The distance may be less than 1 millimeter or greater than 10 millimeters.

In some implementations, it is desirable to have a large source-detector separation and a small sensor head face (e.g., small surface area). The large source-detector separation allows thick bones to be measured and the small sensor face allows a relatively small surface area of bone to be exposed for the sensor head. In these implementations, it may be desirable to position source and detector structures near the edges of the sensor face so that there can be a large source and detector separation.

Thus, in a specific implementation, distances between sensor structures and an edge of the sensor head defining the face of the sensor head are about 1.2 millimeters. The distance may be about 1.5 millimeters or less, but can range from about 0.2 to about 5 millimeters. This includes, for example, 0.3, 0.4, 0.5, 0.6, 0.7, 0.8, 0.9, 1, 1.1, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, or 4.9 millimeters. The distances may be less than 0.2 millimeters or greater than 5 millimeters.

It may be desirable to position a source and a detector such that a longest line across the face of the sensor head has the source at one end of the line and the detector at an opposite end of the line. This allows for a large measurement depth for a given sensor. The longest line may be a diameter if the sensor face has the shape of a circle. The longest line may be diagonal if the sensor face has the shape of a square.

While FIGS. 7-12 show embodiments with two, three, or four sensor openings in the sensor unit, any suitable number of sensor openings can be present in the sensor unit. For example, there may be one, two, three, four, five, six, seven, or eight or more sensor openings. Any one or more sensor openings can be source structures, and any one or more sensor openings can be detector structures. A number of source structures can be equal to a number of detector structures in the sensor unit, or they can be different.

In a specific implementation, a sensor head has an asymmetric arrangement of two source structures and four detector structures. This sensor head may be referred to as an asymmetric 2s4d sensor. In this specific implementation, the four detector structures are arranged on a first line. The first source structure is below the first detector structure of the four detector structures. The second source structure is below the last detector structure of the four detector structures. A distance between the first source structure and first detector structure is different from a distance between the second source structure and last detector structure. The first source structure may be directly below the first detector structure. That is, a second line passing through the first source structure and first detector structure is perpendicular to the first line. The second source structure may be directly below the last detector structure. That is, a third line passing through the second source structure and last detector structure may be perpendicular to the first line.

In other implementations, the first source structure is not directly below the first detector structure. That is, the second line may be oblique to the first line. The second source structure is not directly below the last detector structure. That is, the third line may be oblique to the first line.

In implementations discussed so far in this application, each opening of the sensor head has a single fiber optic cable associated with it. However, in further implementations of the invention, each opening of the sensor head may have multiple fibers optic cables—two or more—associated with it. Or, each opening of the sensor head may have multiple light paths or light channels associated with it.

These light paths can be used simultaneously for transmitting to bone or receiving light from bone. Within a single opening, there may be two source structures, two detector structures, or one source and one detector structure. And for a single sensor head, there may be two or more such openings with multiple light channels.

In other words, in a specific implementation, a single opening on the surface of the sensor head holds a single fiber optic cable that has both source and detector light channels. For example, the single fiber optic cable may be a concentric core fiber having an inner core light channel which is surrounded by an outer core light channel. In this specific implementation, one of the inner core light channel or outer core light channel is a source channel and another of the inner core light channel or outer core light channel is a detector channel.

Sensor head openings having multiple light channels are further discussed in U.S. patent application Ser. No. 12/194,508, filed Aug. 19, 2008, which is incorporated by reference. There are various other implementations of sensor opening patterns which can be incorporated into a sensor unit. Some of these implementations are discussed in U.S. Pat. No. 7,355,688, issued Apr. 8, 2008, U.S. patent application Ser. No. 12/126,860, filed May 24, 2008, U.S. patent application Ser. No. 12/178,359, filed Jul. 23, 2008, and U.S. patent application Ser. No. 12/410,007, filed Mar. 24, 2009. These patent and patent applications are assigned to the same assignee as this patent application and are incorporated by reference.

Figure 13:
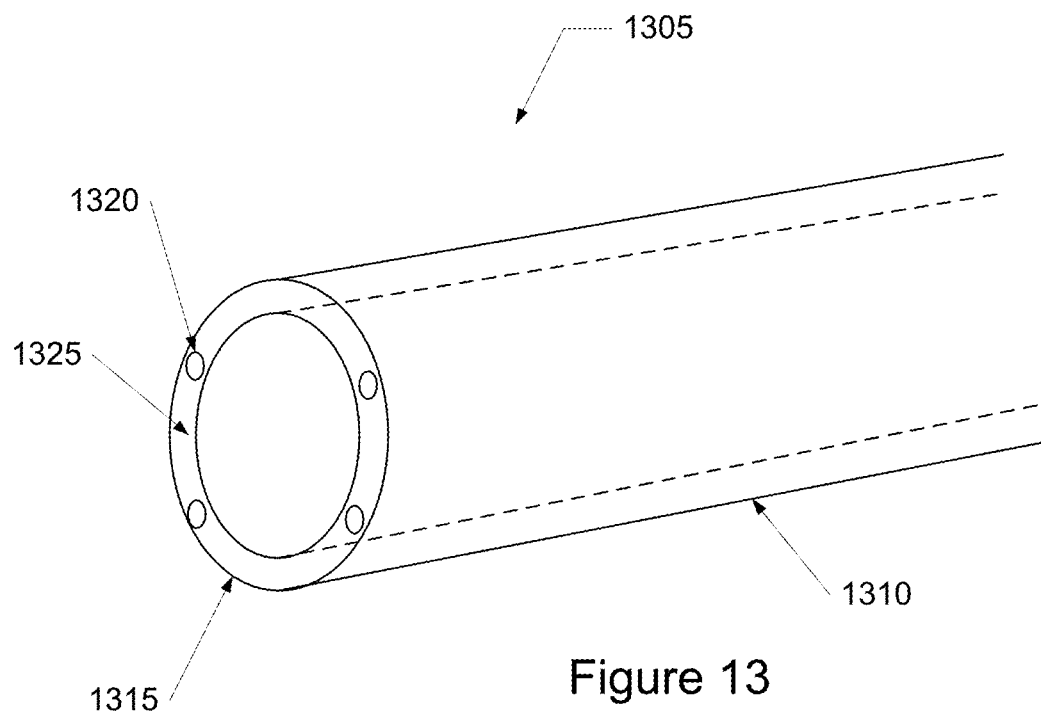
FIG. 13 shows a perspective view of a bone oximeter probe with a sensor unit surrounding a tube of the probe.
Figure 14:
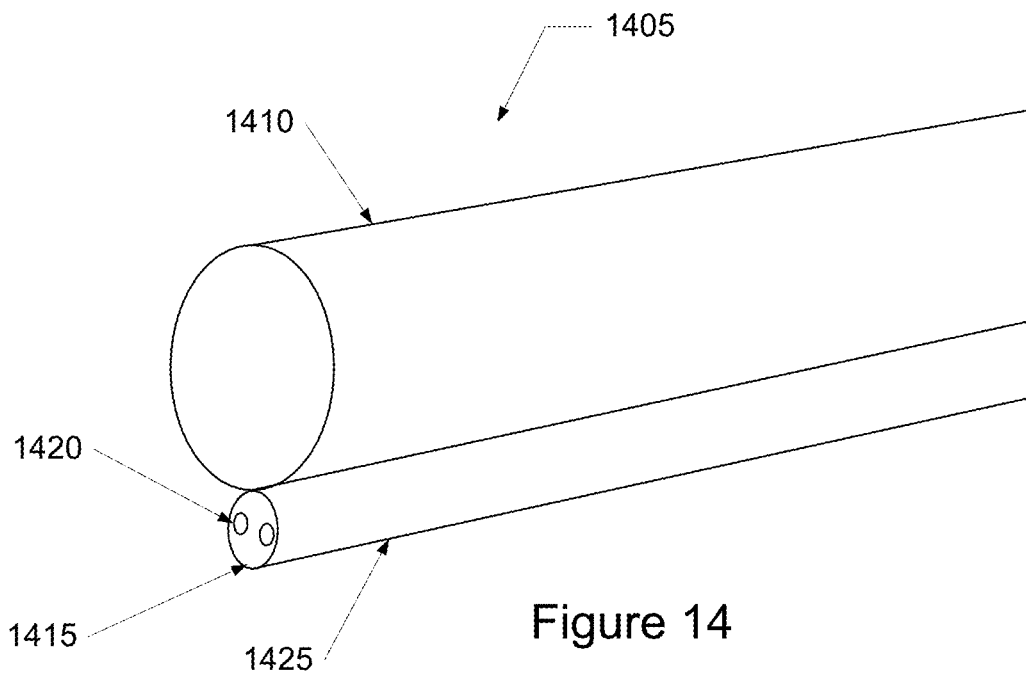
FIG. 14 shows a perspective view of a bone oximeter probe with a sensor unit which is attached to an outer surface of a tube of the probe.

Although FIGS. 7-12 show embodiments of the invention where optical fibers are inside the elongated member, optical fibers may be located elsewhere. FIGS. 13-14 show embodiments in accordance with the present invention where optical fibers are not located inside a lumen or passageway of the elongated member, but are coupled to an outer surface of the elongated member.

FIG. 13 shows a bone oximeter probe 1305 that includes an elongated member 1310 and a sensor probe 1315 which surrounds the elongated member. The sensor probe includes four optical fibers 1320 in a sheath material 1325 which surrounds and holds the optical fibers in their positions. The sheath material may be any suitable biocompatible material such as silicone or polyurethane.

FIG. 14 shows another bone oximeter probe 1405 with an elongated member 1410 and a sensor probe 1415 which is axially aligned with and attached to an outer surface of the elongated member. The sensor probe has two optical fibers 1420 which are surrounded by a sheath material 1425.

In a specific implementation, the elongated member is a solid rod that does not have a passageway or lumen. That is, the elongated member is not hollow. The elongated member as shown, for example, in FIGS. 13-14, may be a solid bar, shaft, stick, or dowel. The elongated member may have a channel or groove extending lengthwise along its outer surface to hold a fiber optic cable. In this specific implementation, the optical fibers are outside the elongated member or attached to an outer surface of the elongated member rather than being inside the elongated member. The elongated member may be a solid rod that has channels or holes extending between opposite ends of the elongated member. Each channel may hold a single conductor or optical fiber cable.

In another specific implementation, the elongated member is hollow or has a passageway or lumen and at least some optical fibers are attached to an outer surface of the elongated member. In this specific implementation, the passageway allows instruments (e.g., surgical tools) to be passed through the passageway. Some examples of instruments include a camera, dissector, grasper, forceps, scissor, needle holder, fan retractor, cautery tools, puncture needle, and K-wire.

FIG. 15 shows another implementation of a bone oximeter probe 1505 where a scanning surface with sensor openings is located on a sidewall of an elongated member 1510 at or near its distal end region. FIG. 16 shows a longitudinal cross section of a tip region 1515 of the probe shown in FIG. 15.

Referring now to FIG. 16, bone oximeter probe 1505 includes a sensor head 1610 which includes distal ends of optical fibers 1615. A sensor unit or sensor head refers to a portion of a device (typically located at a distal end region of the device) which has sensor openings coupled with optical fibers and provides a scanning surface or surfaces to make optical measurements.

In the implementation shown in FIGS. 15-16, four sensor openings 1620 of the bone oximeter probe are located on a sidewall of a distal end region of the elongated member, rather than at the open end of the elongated member at its tip as shown in FIGS. 5-6. The bone oximeter probe shown in FIGS. 15-16 may be referred to as a device with a side-looking sensor array, whereas the probe device shown in FIGS. 5-6 may be referred to as a device with a forward-looking sensor array. A bone oximeter probe with a side-looking sensor array can make measurements of bone where the bone is located adjacent to the sidewall of the elongated member, whereas a bone oximeter probe with a forward-looking sensor array can make measurements where the bone is located in front of the tip of the probe.

As shown in FIG. 16, the distal ends of the optical fibers are coupled to the sensor openings on the side wall of the elongated member. In this implementation, sensor unit 1610 includes optical fibers 1625a-d which are threaded and inserted into four channels which are located on a side wall of elongated member 1510 near its tip. As shown in FIG. 16, the distal ends of the optical fibers are flushed with the outer surface of the elongated member sidewall to provide a side-looking sensor array. In another implementation, the distal ends of the optical fibers are recessed below a surface of the sidewall or project beyond the surface of the sidewall.

The optical fibers may be adhesively attached inside the elongated member to prevent them from moving around. A block (e.g., cylindrical block) 1630 may be used to block the lumen of the elongated member at its tip to prevent tissue debris from entering into the bone oximeter probe during a surgical procedure.

In the implementation shown in FIGS. 15-16, the sensor openings are arranged in a linear array. In one embodiment, the distal ends of optical fibers 1625a-b may be source structures (i.e., first and second source structures, respectively) which transmit light from a light source into bone, and the distal ends of optical fibers 1625c-d may be detector structures (i.e., first and second detector structures, respectively) which detect or collect light reflected from the bone and transmit the reflected light to a photodetector.

In other implementations, sensor openings of the side-looking sensor array may be arranged in the sensor patterns shown in FIGS. 7 and 9-12 and discussed above. There may be more than four sensor openings or less than four sensor openings. For instance, a bone oximeter probe may have multiple sets (e.g., three, four, five, six, or more) of sensor openings in a linear array all the way around the sidewall at a distal end region of the elongated member.

In various specific implementations, a probe with a side-looking sensor array includes a tube having a distal end and a proximal end, opposite the distal end, a set of sensor openings, and a cable extending from the proximal end of the tube. A sidewall of the tube is between the distal and proximal ends. The distal end may be closed or sealed. For example, a plug or block may be inserted into the distal end. The set of sensor openings are on the sidewall tube. The set of sensor openings are closer or nearer to the distal end than the proximal end.

The set of sensor openings may be arranged linearly with respect to an axis passing through the tube. That is, a line passing through the set of sensor openings is parallel to the axis passing through the tube. In this specific implementation, a first sensor opening of the set of sensor openings is nearer to the distal end than a second sensor opening of the set of sensor openings. A length of a first optical fiber connected to the first sensor opening is greater than a length of a second optical fiber connected to the second sensor opening.

The set of sensor openings may be arranged along a circumference of or radially about the tube. In this specific implementation, there are first and second sensor openings of the set of sensor openings. A first distance is from the distal end to the first sensor opening. A second distance is from the distal end to the second sensor opening. The first distance is equal to the second distance. A length of a first optical fiber connected to the first sensor opening is equal to a length of a second optical fiber connected to the second sensor opening.

The set of sensor openings may be arranged along a helix of the tube. In this specific implementation, a first distance is from the distal end of the tube to the first sensor opening. A second distance is from the distal end of the tube to the second sensor opening. The second distance is greater than the first distance. A length of a first optical fiber connected to the first sensor opening is greater than a length of a second optical fiber connected to the second sensor opening.

In other various specific implementations, a probe with a forward-looking sensor array includes a tube having a distal end and a proximal end, opposite the distal end, a set of sensor openings, and a cable extending from the proximal end of the tube. A sidewall of the tube is between the distal and proximal ends. The sidewall is closed and does not have any openings. Rather, it is the distal end that includes a set of openings. Each opening holds a fiber optic cable. The fiber optic cables are straight. That is, the fiber optic cables extend from the proximal end to the distal end without changing direction. For example, there are no bends or angles. Lengths of the fiber optic cables are the same. The fiber optic cables within the tube run in a direction parallel to an axis passing through the tube.

Light directed into the bone via a first fiber optic cable travels in a first direction from the proximal end towards the distal end and exits a first opening in the first direction. Light reflected from the bone enters a second opening in a second direction. The reflected light travels from the distal end towards the proximal end in the second direction and through a second fiber optic cable. The second direction is opposite the first direction.

FIG. 17 shows another implementation of a bone oximeter probe 1705 having a sensor head 1710 which includes distal end portions of two sets of optical fibers—a first set 1715 which forms a forward-looking sensor array and a second set 1720 which forms a side-looking sensor array.

The distal end regions of the first set of optical fibers are aligned along the longitudinal axis of the elongated member, and are inserted into channels of a block 1725. The block may be attached to an inner wall of the elongated member by an adhesive. The distal end portions of the second set of optical fibers are inserted into channels on the sidewall of the elongated member, and the distal ends of the optical fiber are flushed with the outer surface of the elongated member sidewall. If desired, an adhesive may be used to firmly attach the second set of optical fibers inside the lumen of the elongated member. In this implementation, since the bone oximeter probe includes both the forward-looking sensor array and the side-looking sensor array, the probe can make measurements of bone where a bone is in front of the tip of the probe as well where a bone is on a side of the probe.

In a specific implementation, the optical fibers forming the forward-looking sensor array are attached to a first channel (e.g., a receptacle) of the system unit, and the optical fibers forming the side-looking sensor array are attached a second, independent channel (e.g., receptacle) of the system unit. The optical fibers forming the forward looking sensor array and the optical fibers forming the side-looking sensor array may be directly attached to the first channel and second channel, respectively, of the system unit. Alternatively, the proximal end portions of the optical fibers forming the forward-looking sensor array can be coupled to a connector, which then connects the optical fibers to the first channel of the system unit. Also, the proximal end portions of the optical fibers forming the side looking sensor array can be coupled to another connector, which then connects the optical fibers to the second channel of the system unit.

By using separate channels in the system unit, optical signals to and from the fibers of the forward-looking sensor array can be controlled independently from optical signals to and from the fibers of the side-looking sensor array. For example, the optical signals to and from the sensors connected to the first channel will not interfere with those on the second channel, and vice versa. Any signals transferred over the first channel will appear only at the sensors attached to the first channel or at the first channel input of the system unit. Any signals transferred over the second channel will appear only at the sensors attached to the second channel or at the first channel input of the system.

In another implementation, the proximal ends of both sets of optical fibers (i.e., forward-looking sensor and side-looking sensor) can be attached to a single connector, which can then be connected to a single channel of the system unit. It may be desirable to use a single connector for all of the optical fibers and attach the connector to a single channel of the system unit to reduce cost, if the total number of optical fibers included in a bone oximeter probe is not too large (e.g., eight or less).

Figure 18:
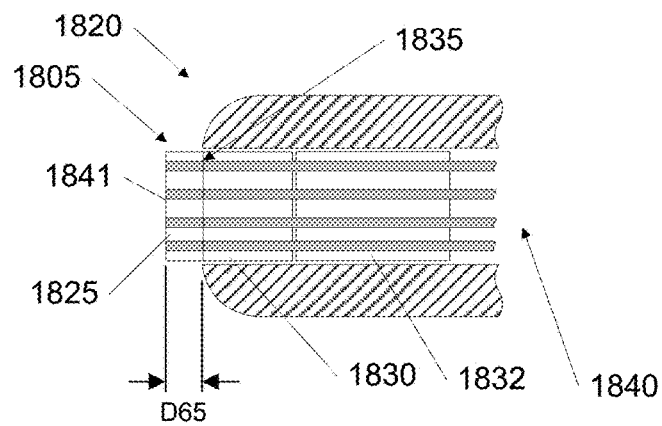
FIG. 18 shows a longitudinal cross-sectional view of a tip of a probe having a deformable sensor head.

FIG. 18 shows a longitudinal cross section of a tip of a bone oximeter probe 1805. This probe includes a sensor head 1820 that is deformable or has a deformable surface. This specific implementation of the sensor head includes a soft deformable block 1830 and a solid un-deformable (or nondeformable or nondeforming) block 1832 (to hold the fibers separated as shown). A distance D65 indicates the distance or length of a portion 1825 of the deformable block that is outside the elongated member or protrudes out from the distal end of the elongated member.

The sensor head includes a set of channels 1835 for a set of fiber optic cables 1840. In a specific implementation, a channel is continuous through the nondeformable block and the deformable block. In other words, there is a single channel extending through the nondeformable block and the deformable block.

In another implementation, the channel is discontinuous. For example, a gap or space may be between the nondeformable block and the deformable block. In this specific implementation, the nondeformable block includes a first channel and the deformable block includes a second channel. In a specific implementation, an end of the first channel faces an end of the second channel so that a single fiber optic cable can pass through the first channel, span the gap between the nondeformable block and the deformable block, and continue through the second channel. In another implementation, an end of the first channel faces an end of the second channel. The first channel holds a first fiber optic cable and the second channel holds a second fiber optic cable. Light passing through the first fiber optic cable in the first channel can continue through into the second fiber optic cable in the second channel.

In a specific implementation, the fibers reach the very end of the deformable block 1830. That is, the fibers extend to a surface 1841 of the deformable block. Surface 1841 may be referred to as a bone facing surface or bone contacting surface. Ends of the fibers are flush with surface 1841. In other words, surface 1841 lies in a plane and ends of the fibers lie or are on the plane (i.e., same plane).

In other implementations, the fibers terminate before reaching the surface or the fibers extend past the surface. An implementation may have one or more fibers which are flush with the surface, one or more fibers which terminate before reaching the surface, one or more fibers which extend past the surface, or combinations of these.

An adhesive, such as epoxy, may be used to connect or secure the deformable block and nondeformable block together. The deformable block may be referred to as a pad, cushion, pillow, adapting pad, or conforming pad. The deformable block may be made of any material that is flexible, springy, elastic, compliant, or pliable. For example, the deformable block may be made of foam (e.g., polyethylene foam), silicon, rubber, neoprene, or a gel. The deformable block can be of any length. For example, the length of the deformable block may range from about 3 millimeters to about 10 millimeters. This includes, for example, 3.5, 4, 4.5, 5, 5.5, 6, 6.5, 7, 7.5, 8, 8.5, 9, 9.5, or 9.9 millimeters. The length may be less than 3 millimeters or greater than 10 millimeters.

The nondeformable block may be made of material that is different from a material of the deformable block, such as a rigid material. The nondeformable block may be made of materials similar to that of block 610 (FIG. 6), such as aluminum (e.g., 6061 aluminum).

In a specific implementation, a length of the nondeformable block is greater than a length of the deformable block. In other implementations, the length of the nondeformable block is less than a length of the deformable block. The length of the nondeformable block may be equal to a length of the deformable block.

In FIG. 18 a portion of the deformable block is inside the elongated member (i.e., inside a passageway of the elongated member). In other implementations, the deformable block is completely outside of the elongated member. For example, in a specific implementation, the nondeformable block extends to the edge of the elongated member, is flush with the edge, or extends past the edge. The deformable block is attached to the nondeformable block and is outside the elongated member.

In a specific implementation, surface 1841 of the deformable block is flat or planar. In other implementations the surface is not flat. For example, the surface can be curved convex or concave as shown in FIGS. 21-24 in order to match or conform to the surface of the bone to be measured.

Figure 19:
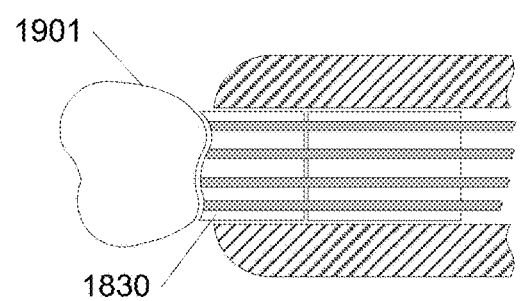
FIG. 19 shows a side view of the probe of FIG. 18 being pressed against a bone.

FIG. 19 shows a longitudinal cross section of the bone oximeter probe of FIG. 18 being placed against a bone 1901. The surface of this bone is not flat. Rather, the surface of this bone includes curves and other anatomical features. Deformable block 1830 can compress or deform around these features as shown in FIG. 19 so that there is good contact between the sensor head and the surface of the bone.

The deformable block allows accurate bone measurements to be made on bone surfaces that include various anatomical features (e.g., ridges, bumps, valleys, and protrusions) because the deformable block helps to seal the sensor head against the surface of the bone. Thus, light from the source fibers is directed into the bone rather than being scattered outside the bone. Similarly, the detector fibers can detect light reflected from the bone rather than ambient light.

In other words, when the sensor head is placed against a bone, the deformable block can deform and adapt to the various surface features or contours of the bone. This helps to ensure that more of the light which is transmitted out of the sensor head is transmitted into the bone and that more of the light which is then reflected from the bone is received at the sensor head.

Some specific examples of anatomical features of a bone include the articular process, articulation, canal, condyle, crest, eminence, epicondyle, facet, foramen, fossa, fovea, labyrinth, line, malleolus, meatus, process, ramus, sinus, spine, suture, trochanter, tubercle, and tuberosity.

In a specific implementation, the optical fibers are designed to flex, bend, or slide within the channels, passageway of the elongated member, or both as the deformable block is compressed. For example, the optical fibers may be threaded through the channels, but not fixedly secured within the channels so that the optical fibers can slide. Alternatively, the optical fibers may be partially secured within the channels such as with an adhesive at a proximal end of the channel and no adhesive at a distal end of the channel.

Referring now to FIG. 18, distance D65 ranges from about 1 millimeter to about 2 millimeters. This includes, for example, 1.1, 1.2, 1.3, 1.4, 1.5, 1.6, 1.7, 1.8, or 1.9 millimeters. Distance D65 may be less than 1 millimeter or greater than 2 millimeters. In other implementations, distance D65 ranges from about 0.5 millimeters to about 5 millimeters. Typically, the thicker the deformable block (i.e., a greater distance D65), the more that the block can compress. Thus, thicker blocks may be used where the surface of the bone is particularly bumpy or has tall ridges and deep valleys. A thicker block may be better able to conform to the taller ridges and deeper valleys of a bone surface as compared to a thinner block. Although FIG. 18 shows a portion of the deformable block protruding from the elongated member, this is not always the case. In other implementations, the deformable block does not protrude from the elongated member. For example, the deformable block may be flush with the distal end of the elongated member. Alternatively, the deformable block may be recessed within the distal end of the elongated member.

FIGS. 20-24 show various specific implementations of sensor heads having surfaces (or pre-formed surfaces) designed to adapt to the various anatomical features that a bone may have. For example, the surface of a bone could be flat, concave, or convex. For flat bone surfaces, the sensor head shown in FIGS. 5-6 may be desirable. This sensor head is flat or planar. An angle between the surface of the sensor head and an axis passing through the elongated member is about 90 degrees or is perpendicular. This sensor head may be placed on bone surfaces that are flat, such as the flat, broad vertebral spinous process bone.

In contrast, for bone surfaces that are concave or convex, the sensor heads shown, for example, in FIGS. 21-24 may be more desirable than the sensor head shown in FIGS. 5-6. These sensor heads may be placed on bones that curved such as the curved aspects of the laminar plates. The curved surfaces of these sensor heads can make better contact (e.g., full flat contact) with curved bone surfaces as compared to the flat sensor heads of FIGS. 5-6.

Figure 20:
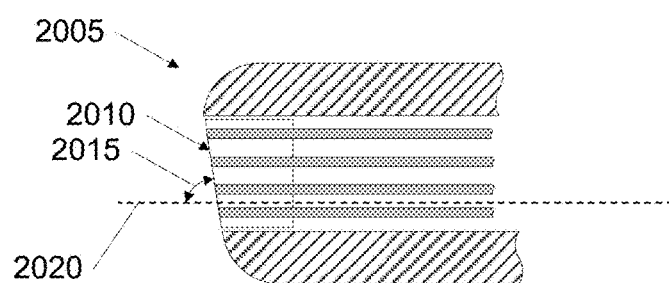
FIG. 20 shows a longitudinal cross-sectional view of a tip of a probe having an angled sensor head.

FIG. 20 shows a side view of a sensor head 2005 having a slanted or angled surface 2010. This probe can be held at an oblique angle relative to a surface of the bone if, for example, the physician is unable to hold the probe orthogonal to the surface of the bone.

An angle 2015 is between surface 2010 and an axis 2020 which passes through the elongated member and the surface. The angle is less than 90 degrees. For example, the angle may be about 30, 45, or 60 degrees. The angle may range from about 30 degrees to about 89 degrees. The angle may be less than 30 degrees or greater than 89 degrees (e.g., 89.9 degrees).

Figure 21:
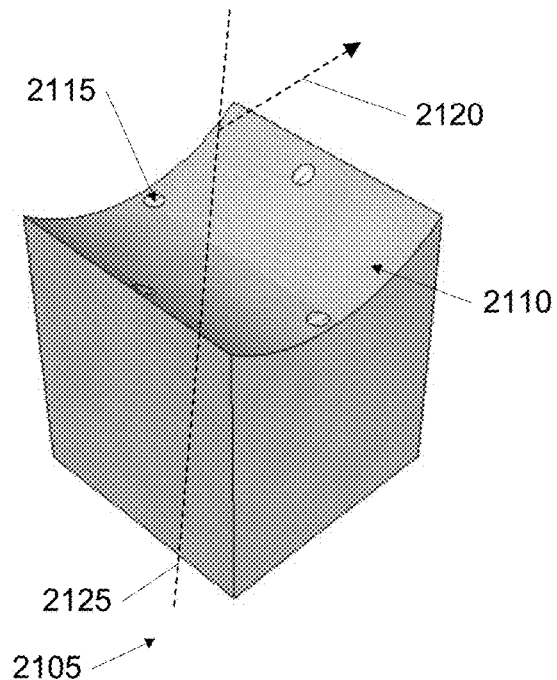
FIG. 21 shows a perspective view of a sensor head that is concave in one direction.

FIG. 21 shows a perspective view of a sensor head 2105 having a concave surface 2110. The surface includes source and detector structures 2115. The surface is concave in a first or single direction 2120. The first direction is perpendicular (i.e., orthogonal) to an axis 2125 passing though the elongated member and surface. This surface can complement a convex feature or surface of the bone to be measured, such as a cylindrical portion of the bone.

Figure 22:
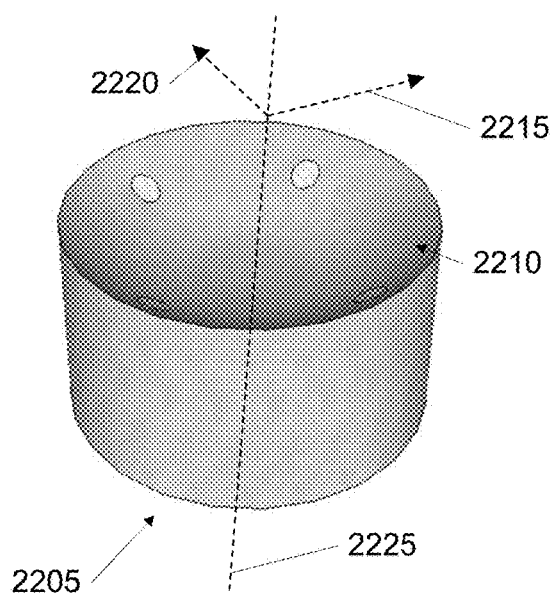
FIG. 22 shows a perspective view of a sensor head that is concave in two directions.

FIG. 22 shows a perspective view of a sensor head 2205 having a concave surface 2210. This sensor head is similar to the sensor head shown in FIG. 21, but this sensor head is concave in two directions—a first direction 2215 and a second direction 2220. That is, the surface is bowl-shaped. The first direction is perpendicular to the second direction. The first and second directions are perpendicular to an axis 2225 passing through the elongated member and surface. This surface can complementation a convex feature or surface of the bone to be measured, such as a ball-shaped portion of the bone.

Figure 23:
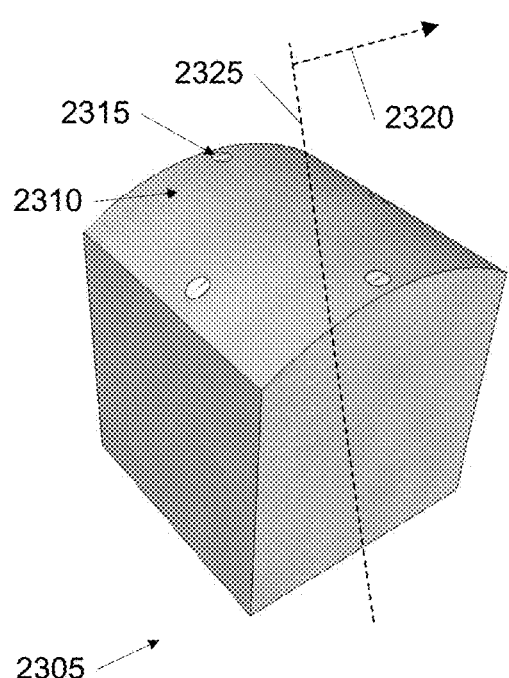
FIG. 23 shows a perspective view of a sensor head that is convex in one direction.

FIG. 23 shows a perspective view of a sensor head 2305 having a convex surface 2310. The surface includes source and detector structures 2315. The surface is convex in a first or single direction 2320. The first direction is perpendicular to an axis 2325 passing through the elongated member and surface. This surface can complement a concave feature or surface of the bone to be measured, such as a grooved portion of the bone.

Figure 24:
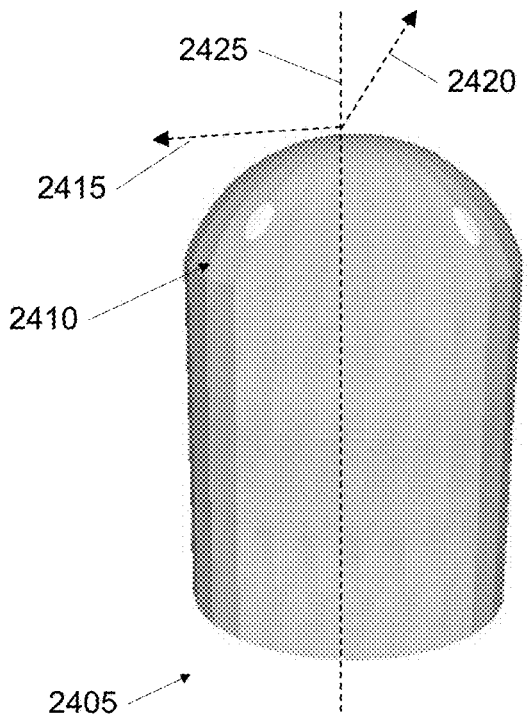
FIG. 24 shows a perspective view of a sensor head that is convex in two directions.

FIG. 24 shows a perspective view of a sensor head 2405 having a convex surface 2410. This sensor head is similar to the sensor head shown in FIG. 23, but this sensor head is convex in two directions—a first direction 2415 and a second direction 2420. That is, the surface is dome shaped. The first direction is perpendicular to the second direction. The first and second directions are perpendicular to an axis 2425 passing through the elongated member and the surface.

This surface can complement a concave feature or surface of the bone to be measured, such as a socket-shaped portion of the bone.

Figure 25:
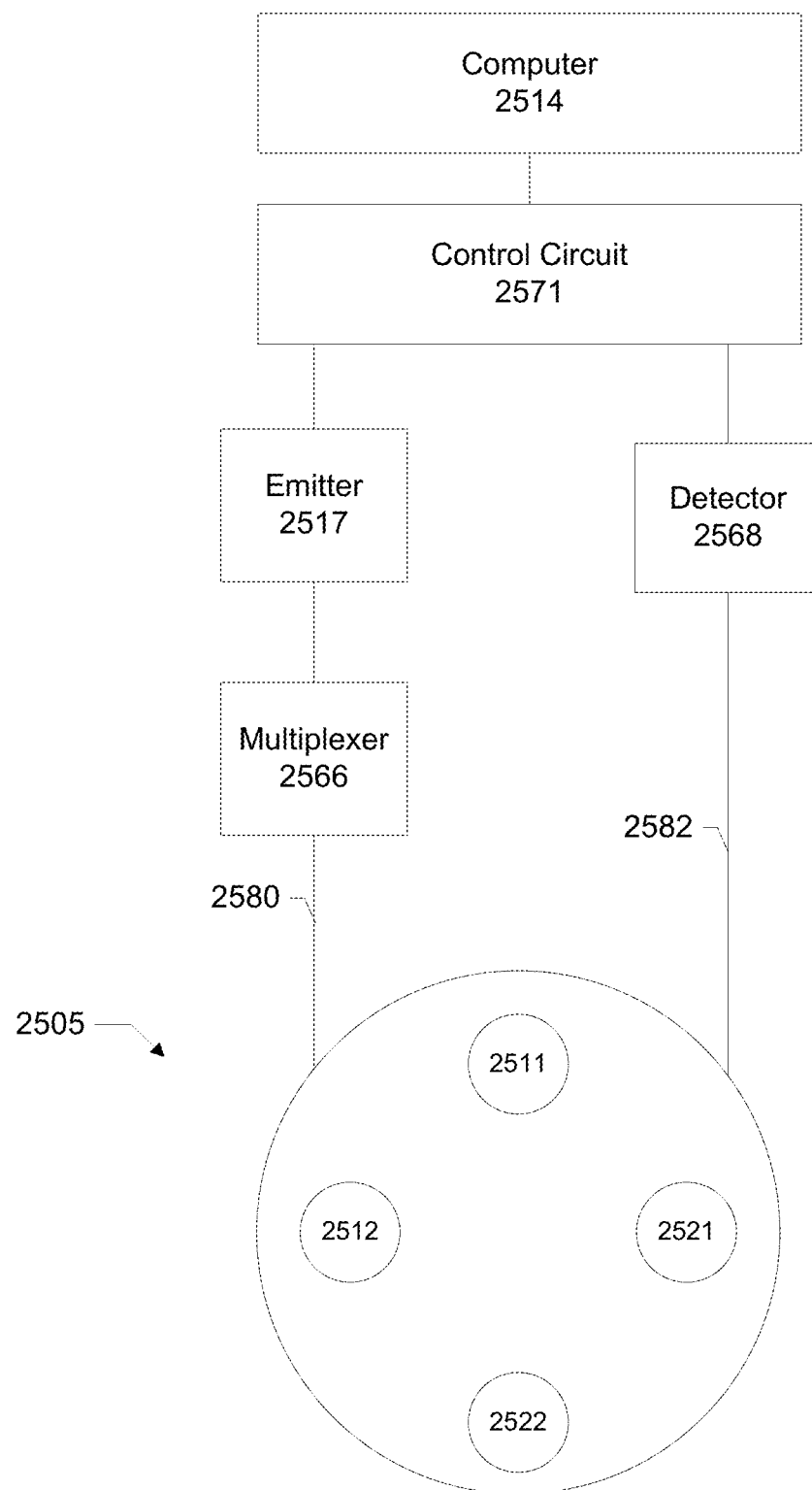
FIG. 25 shows a block diagram of a bone oximeter system that includes a multiplexer.

FIG. 25 shows a block diagram of a specific implementation of the invention. A bone oximeter probe 2505 is attached to other components of a bone oximeter system. The probe has sensors 2511-2512 that are each connected to an output of a multiplexer 2566. The multiplexer is connected to an emitter 2517 which is connected to a control circuit 2571 which is connected to a computer 2514. Sensors 2521-2522 are connected to a detector 2568 which is connected to the computer via the control circuit.

The computer controls operation of the bone oximeter probe. To make a measurement using particular source and detector structures, the computer controls the emitter to emit radiation through source structures 2511-2512. This radiation is transmitted into the bone being evaluated and transmitted or reflected back into detector structures 2321-2322. The computer, via the multiplexer, controls which source structure to use to transmit the radiation. For example, the computer can control the control circuit to select the output of the multiplexer corresponding to source structure 2511. Then, radiation is transmitted through source structure 2511 and is not transmitted through source structure 2512 because the multiplexer prevents or blocks the transmission.

The computer receives data about the received radiation from the detector circuit, and using information about the transmitted radiation, performs calculations to determine an oxygen saturation measurement.

Using the circuitry of FIG. 25, a user makes measurements using detector structures at varying distances with respect to the source structures. This information is used in making oximeter measurements at various or specific depths in the bone. The depth of light penetration into the bone is proportional to the distance of the detector structure from the source structure.

Although the circuitry shown is for the implementation where the computer via the multiplexer controls which source structures to use, one of skill in the art can make the necessary changes so that the computer via the multiplexer controls instead which detector structures to use. In short, the detector and source structures are swapped and the emitter and detector are swapped. Thus, in a specific implementation, structures 2511-2512 are detector structures connected to the computer via the detector. Structures 2521-2522 are source structures connected to the computer via the emitter. The multiplexer is connected to the computer through the detector.

In this specific implementation radiation is emitted through the source structures. The computer via the multiplexer chooses which detector structure to use in making an oxygen saturation measurement. The multiplexer can block or prevent the transmission of reflected radiation from a specific detector structure. The reflected radiation that the multiplexer transmits from the chosen detector structure and the spacing between the chosen detector structure and source structures is then used to determine an oxygen saturation measurement.

Multiplexer 2566 is representation of a component that performs the multiplexing function. The multiplexer may be implemented using electrical components (such as transistors, resistors, integrated circuits, and the like) or may be implemented mechanically (such as using switches, gears, pulleys, and the like). The multiplexer may also be implemented using optical fiber, microelectromechanical systems (MEMs), mirrors, and the like. The invention may use any technique, circuit, or device that provides a multiplexing function in order to selectively receive input from (or output to) some structures connected to the multiplexer, but not others.

Signals 2580 and 2582 can be optical signals, electrical signals, or both. For example, if the structures include optical fiber then the signals will be optical signals. If the structures include LEDs or photodiodes then the signals will be electrical signals.

In an implementation signal 2580 is an optical signal and structures 2511-2512 are source structures including optical fiber. In another implementation signal 2580 is an electrical signal and the source structures include LEDs.

In an implementation signal 2580 is an optical signal and structures 2521-2522 are detector structures including optical fiber. In another implementation, signal 2582 is an electrical signal and the detector structures include photodiodes. In a specific implementation, signal 2580 is an optical signal and signal 2582 is an electrical signal. In this specific implementation, structures 2511-2512 include optical fiber and structures 2521-2522 include photodiodes. In another specific implementation, signal 2580 is an electrical signal and signal 2582 is an optical signal. In this specific implementation, structures 2511-2512 are source structures that include LEDs and structures 2521-2522 are detector structures that include optical fiber. Multiplexing is further discussed in U.S. patent application Ser. No. 12/359,792, filed Jan. 26, 2009, which is incorporated by reference.

Figure 26:
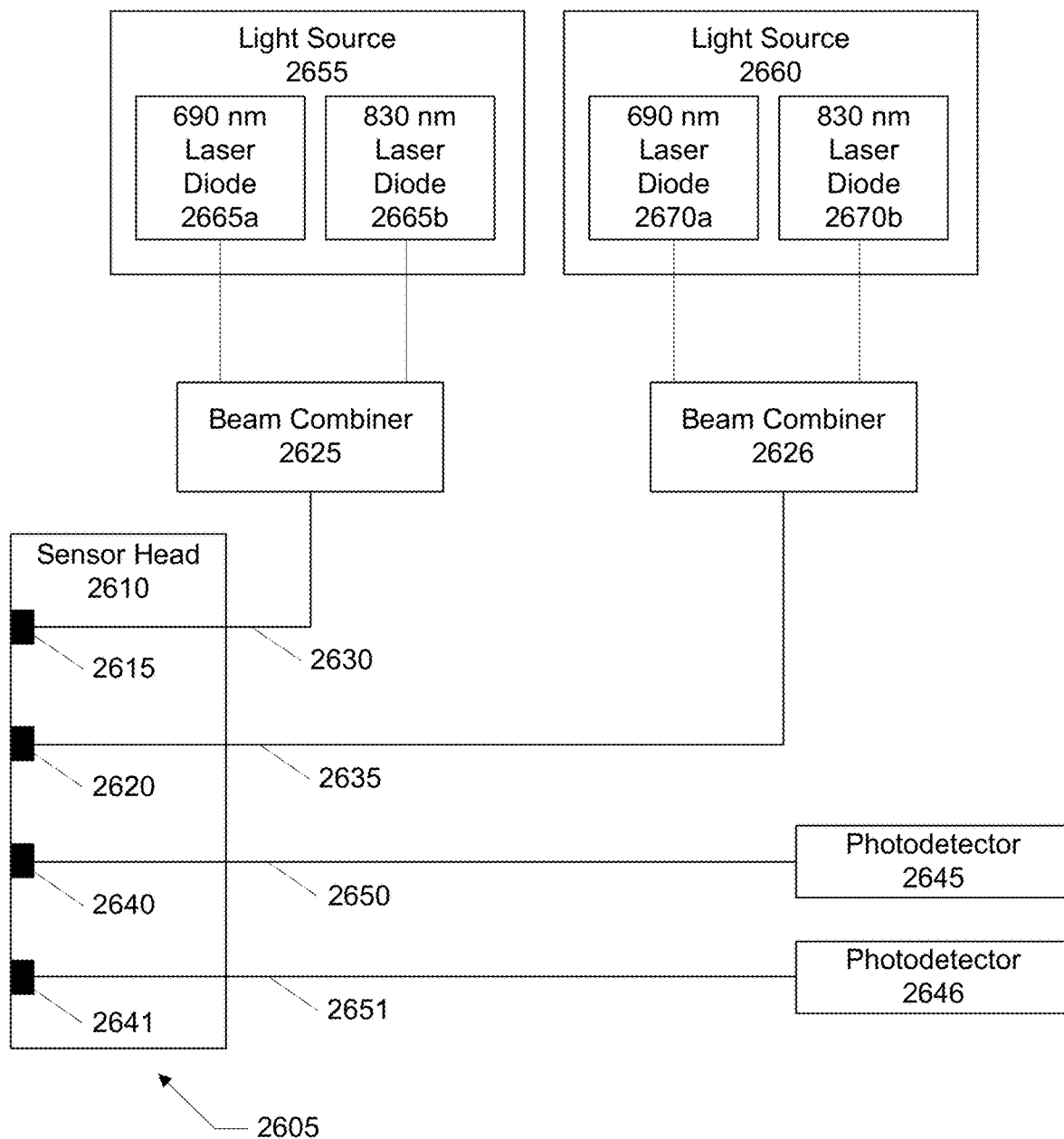
FIG. 26 shows a block diagram of a bone oximeter system that includes a beam combiner.

FIG. 26 shows a block diagram of a specific implementation of the invention. A bone oximeter probe 2605 has a sensor head 2610 with first and second source structures 2615 and 2620 that are connected to first and second beam combiners 2625 and 2626 via first and second optical fibers 2630 and 2635. The sensor head also has detector structures 2640-2641 that are connected to photodetectors 2645-2646 via optical fibers 2650-2651. The beam combiners have inputs to receive optical signals from first and second light sources 2655 and 2660. More specifically, the first light source includes a first 690-nanometer laser diode 2665$a$ and a first 830-nanometer laser diode 2665$b$. The second light source includes a second 690-nanometer laser diode 2670$a$ and a second 830-nanometer laser diode 2670$b$.

The beam combiner receives various wavelengths of light from the laser diodes and outputs the light to the source structures. The beam combiner can be used to allow a single output fiber to carry different wavelengths of light. In brief, to make measurements using the circuitry shown in FIG. 26:

1. The first beam combiner receives a 690-nanometer wavelength of light from the first light source and outputs the light onto the first optical fiber.

2. The second beam combiner receives a 690-nanometer wavelength of light from the second light source and outputs the light onto the second optical fiber.

3. The first beam combiner receives an 830-nanometer wavelength of light from the first light source and outputs the light onto the first optical fiber.

4. The second beam combiner receives an 830-nanometer wavelength of light from the second light source and outputs the light onto the second optical fiber.

A more detailed discussion of the operation is as follows: In a first step, the first light source (or 690-nanometer laser diode of the first light source) produces a 690-nanometer wavelength of light that is transmitted to the first beam combiner. The first beam combiner outputs the 690-nanometer light onto the first optical fiber, through the first source structure, and into the bone. The photodetectors detect the reflected 690-nanometer light from the bone. During the first step, the other laser diodes (i.e., diodes 2665$b$ and 2670$a$-$b$)

remain off. Alternatively, the first beam combiner, second beam combiner, or both can block light from the other laser diodes so that the light is not transmitted through the source structures. A multiplexer or multiplexing operation, as shown in FIG. 25 and discussed above, may be used to block the light.

In a second step, the second light source (or 690-nanometer laser diode of the second light source) produces a 690-nanometer wavelength of light that is transmitted to the second beam combiner. The second beam combiner outputs the 690-nanometer light onto the second optical fiber, through the second source structure, and into the bone. The photodetectors detect the reflected 690-nanometer light from the bone. During the second step, similar to the first step, the other laser diodes (i.e., diodes 2665a-b and 2670b) remain off or the beam combiners block the light from the other laser diodes.

In a third step, the first light source (or 830-nanometer laser diode of the first light source) produces an 830-nanometer wavelength of light that is transmitted to the first beam combiner. The first beam combiner outputs the 830-nanometer light onto the first optical fiber, through the first source structure, and into the bone. The photodetectors detect the reflected 830-nanometer light from the bone. During the third step, similar to the first step, the other laser diodes (i.e., diodes 2665a and 2670a-b) remain off or the beam combiners block the light from the other laser diodes.

In a fourth step, the second light source (or 830-nanometer laser diode of the second light source) produces an 830-nanometer wavelength of light that is transmitted to the second beam combiner. The second beam combiner outputs the 830-nanometer light onto the second optical fiber, through the second source structure, and into the bone. The photodetectors detect the reflected 830-nanometer light from the bone. During the fourth step, similar to the first step, the other laser diodes (i.e., diodes 2665a-b and 2670a) remain off or the beam combine block the light from the other laser diodes.

It should be appreciated that these steps can occur in any order. For example, the first and second steps may be swapped. The 830-nanometer wavelength of light may be transmitted into the bone before the 690-nanometer wavelength of light is transmitted into the bone.

Thus, with the beam combiner, a single output fiber (e.g., first optical fiber 2630), can be used to output via a source structure (e.g., first source structure 2615) light of a first wavelength (e.g., 690 nanometers) and light of a second wavelength (e.g., 830 nanometers), different from the first wavelength. That is, at a first time, the source structure outputs light of the first wavelength. At a second time, different from the first time, the source structure outputs light of the second wavelength.

The use of a beam combiner allows for a small and compact sensor head (i.e., small sensor head surface area) because it allows a single fiber to output different wavelengths of light, thus removing the need to have multiple output fibers at the sensor head, each dedicated to outputting a specific wavelength of light. Small sensor heads can be more desirable than large sensor heads because the small sensor heads can be advanced through small incisions to the underlying bone. Small incisions are generally more desirable than large incisions because with small incisions there is less blood loss for the patient. There can also be shorter recuperation times, less pain, and less scaring with small incision as compared to large incisions.

In a specific implementation, the first beam combiner, second beam combiner, or both are external to the probe and are inside a system unit or console of the bone oximeter system such as console 303 shown in FIG. 3. That is, the beam combiners and light sources are all contained in a single container, i.e., console 303. In another implementation, the first beam combiner, second beam combiner, or both are external to the probe and to the console. In this specific implementation, the beam combiners are connected between the console and the probe. For example, the beam combiners may have an input port that is connected to the console and an output port that is connected to the probe. The input port allows the beam combiner to receive optical signals from the console. The output port allows the beam combiner to output the received light to the probe.

Some embodiments will not have a beam combiner. For example, instead of a single shared fiber, an optical fiber may connect a source structure to a laser diode directly instead of connecting the source structure to a beam combiner. Not having a beam combiner can reduce the cost of the oximeter system. Although FIG. 26 shows two beam combiners, an embodiment may have a single beam combiner to, for example, reduce cost. In this specific embodiment, the second beam combiner shown in FIG. 26 is eliminated. Second optical fiber 2635 is connected to the 690-nanometer laser diode of the second light source. The probe may include a third source structure to hold an end of a third optical fiber which connects to the 830-nanometer laser diode of the second light source.

Thus, it should be appreciated that a bone oximeter system can have any number of beam combiners including zero or no beam combiners depending on factors such as desired cost and desired sensor head size. For example, if a higher priority is given to cost as compared to sensor head size, an implementation may include no beam combiners to lower the cost of the system. Conversely, if a higher priority is given to a sensor head size as compared to cost, an implementation may include beam combiners to help reduce the size of the sensor head.

In the example shown in FIG. 26, the beam combiners each have two inputs and one output (i.e., 2-to-1). But, a beam combiner can have any number of inputs and any number of outputs (e.g., four inputs and two outputs or 4-to-1). However, the cost of a beam combiner generally increases with an increasing number of inputs and outputs. Thus, in some cases it will be more economical to select two 2-to-1 beam combiners as compared to selecting a single 4-to-1 beam combiner. In other cases, a single 4-to-1 beam combiner may be selected over two 2-to-1 beam combiners if, for example, the 4-to-1 beam combiner is smaller than two 2-to-1 beam combiners and a small console size is a high priority.

Figure 27:
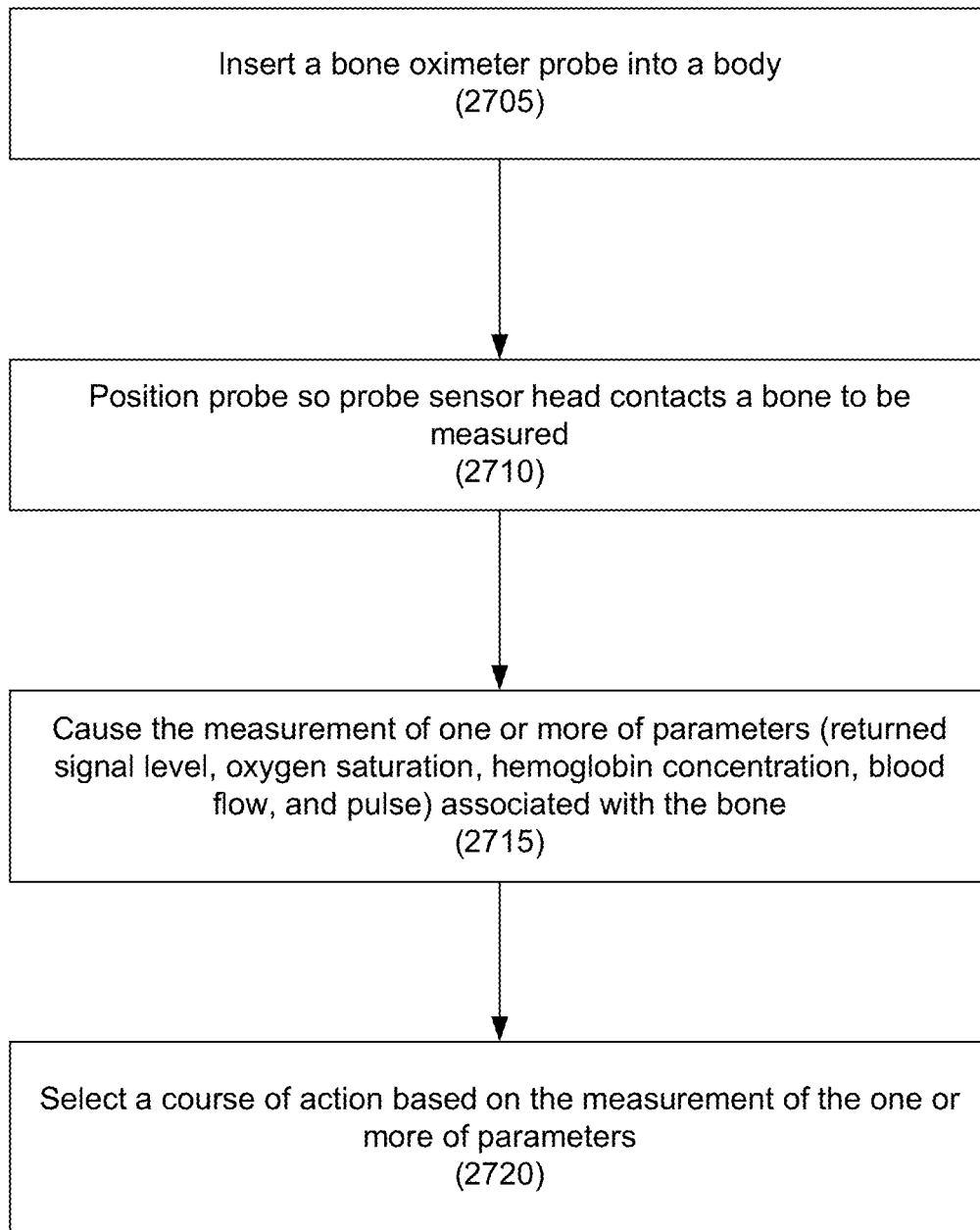
FIG. 27 shows a flowchart of advancing a bone oximeter probe into tissue to obtain bone measurements.

FIG. 27 shows a flowchart for making an oxygen saturation measurement for a bone. In a step 2705, a bone oximeter probe is inserted into a body through an incision. The tip of the probe is directed towards a target bone. In a specific implementation, the probe is inserted by a surgeon who holds the probe. In another specific implementation, the probe is inserted into the body by a robot or a robotic arm. The probe can be visualized inside the body using X-ray, ultrasound, or other visual aid techniques. The tip of the probe may include a camera and lights for the camera so that probe's advancement into the incision can be seen on a video monitor. Alternatively or additionally, when the tip of the probe reaches its target location (e.g., target bone), the surgeon can feel or the robot can detect the resistance in the probe when the sensor head contacts or hits the target bone.

In a step 2710, the doctor positions the probe so that the probe sensor head contacts or is near the target bone to be measured. For example, the doctor may angle or adjust the probe within the incision so that the surface of the sensor head makes good contact with the surface of the target bone.

In a step 2715, the doctor causes the measurement of one or more of parameters associated with the target bone. Some examples of measurement include returned signal level, oxygen saturation, hemoglobin concentration, blood flow, and pulse.

In a specific implementation, the doctor activates the bone oximeter console (e.g., turns on console) so that a first light signal is transmitted in a first direction from the console, through the bone oximeter probe (e.g., through a first fiber optic cable of the probe), and into the target bone. The doctor maintains a position of the probe at the bone so that the probe can receive a reflection of the first light signal from the bone (i.e., a second light signal). The second light signal is transmitted via a second fiber optic cable in a second direction, opposite the first direction, to the console. A calculation is made at the console based on the first and second light signals. The calculation or a value or bone measurement based on the calculation may be displayed on an electronic display of the console for the doctor to read.

In other words, light is transmitted through optical fibers of the bone oximeter probe through openings in the sensor unit located at the tip of the probe. Light scatters in a bone located at or nearby the tip of the probe, and reflected light is detected by the sensor unit, which is returned to a monitoring console. Based on the initial light and the reflected light information, the console can measure and calculate various parameters associated with the bone. These parameters include a signal level of returned light, an oxygen saturation level, a total hemoglobin concentration, a blood flow, and a pulse.

In a step 2720, the doctor selects a course of action based on one or more of the measured parameters. The specific course of action may vary widely depending on, for example, what specific parameter was measured, the patient's condition, health, or age, and so forth. For example, immature skeletons (e.g., persons less than 19 years old) may be more oxygenated than mature skeletons (e.g., persons older than 65 years old).

In a specific implementation, the parameter is a signal quality measurement. The doctor can determine whether the signal quality is sufficient (i.e., there is good contact between the sensor head and the bone) or whether the signal quality is insufficient. If the signal quality is sufficient the doctor may decide to continue monitoring at that specific location on the bone. If the signal quality is insufficient the doctor may reposition the probe at a different location on the bone and make another signal quality measurement to determine whether that different location is suitable to make an oxygen saturation measurement of the bone.

In another specific implementation, the parameter provides an indication of the health of the bone. The measured parameter may be a tissue oxygenation value of the bone, a hemoglobin concentration value of the bone, or both. These values or bone measurements can be used in bone surgery to determine whether one course of action is more appropriate or desirable than another course of action. For example, bone fractures or breaks may be repaired using pins, nails, screws, plates, bioresorbable materials, anchors, and other types of hardware. The bone oximeter provides the surgeon with objective measurements on the health of the bone and can help the surgeon decide which type of hardware, surgical procedure, or both is appropriate for the patient.

Surgeons performing spine bone surgery, such as spine fusion surgery, may use the information provided by the bone oximeter to help them decide upon a method of fusion. The rates of spine fusion surgery have been increasing rapidly over the last 20 years with almost a fourfold increase in rates between 1992 and 2003 (0.3 per 100,000 to 1.1 per 100,000). There were about 575,000 spinal surgery discharges in the United States in 2005 with about 331,000 of these involving fusions. A non-solid fusion or pseudarthrosis is associated with a poor outcome for the patient and can lead to further expense in the future with revision surgeries.

One method of promoting fusion is to place bone graft in the fusion site and the incorporation of this is an interaction between graft and host characteristics. Autogenous bone grafts make use of the special immunogenic status and better vascularity of donor site bone stock and can be well incorporated by the spine. They are generally taken from the iliac crest and as well as being limited in quantity, graft site related morbidity has been estimated at up to 20 percent for autogenous grafts, and so there is also a need for allografts and bone substitutes. One of the most studied and frequently used biologic alternatives to auto graft is bone morphogenetic protein (BMP). The application kit for the rhBMP-2ACS costs about $5000 and is generally paid by the hospital.

Currently, the decision about which of these grafts to use is based on the surgeon's opinion of the risk factors for bone quality. This bone oximeter can provide an objective measurement of the quality of bone by its StO2 and can make selection of bone graft more consistent and quantifiable. With these measurements, the surgeon is better informed as to whether it is necessary to use the expensive BMP graft or whether there is sufficient vascularity in the bone for standard (and cheaper) grafts such as cadaveric allograft ($800). A bone that is well oxygenated may incorporate a standard bone graft such as an allograft which is less expensive than a BMP graft.

Assessment of bone quality would also help to ensure that correct grafts are chosen for each patient, increasing the likelihood of a solid fusion and so reducing the frequency of pseudarthrosis. A further saving of measuring bone quality is that the cost of fusion and then revision following pseuadarthrosis is around $127,000 compared to $75,000 for surgery using BMP and a much lower probability of revision. The correct selection of grafts can save money both in cases of over use of expensive options and also in the consequences of their underuse.

As further background, the biological sequence of bone graft incorporation starts with haematoma formation and release of growth factors. Inflammation occurs and there is a migration and proliferation of mesenchymal cells around the graft site. Vessels invade the graft followed by focal osteoclastic resorption of donor bone. Finally intramembranous, endochondral bone formation, or both occurs on the graft surfaces and remodeling begins to provide structural support.

The decision about which graft will be used is typically based on the surgeon's opinion and their consideration of risk factors for bone vascularisation, as without good vascularity bone graft incorporation is slow and there is an increased chance of pseudarthrosis. The factors influencing the surgeon's decision include age, with pseudarthrosis rates of around 2-3 percent reported in children as opposed to up to 43 percent in adults. Smoking is also a strong predictor with heavy smoking and nicotine reducing bone vascularization. Any local neoplastic process will lead to abnormal new bone formation at the site including both benign and malignant growths. Intense irradiation of an area will reduce vascularization through scarring in a similar way to sclerotic bone from previous fusions. Osteopenic bone may mechanically be unable to support supplemental material if it must bear load. Systemically anti-inflammatory agents and glucocorticoids will also have the effect of suppressing bone remodeling.

Other factors that can affect bone oxygenation include medications (e.g., non-steroidal anit-inflamatory drugs or NSAIDs), steroids, osteopenia (e.g., bone densitometry record or DEXA record), cardiovascular disease, chronic obstructive pulmonary disease (e.g., COPD), asthma, diabetes, radiation, previous spinal fusions, or combinations of these.

Measurements for the bone can be performed at or near the time of surgery. The bone oximeter can detect and continuously monitory hypoxic changes in bone. Tissue oxygenation differences between normal and hypoxic bone may be about 15-20 percentage points in the presence of a stable hemoglobin concentration. This difference may be seen after about 20 minutes.

It should be understood that the specific flow example shown in FIG. 27 is not limited to the specific flows and steps shown. A flow of the invention may have additional steps (not necessarily described in this application), different steps which replace some of the steps presented, fewer steps or a subset of the steps presented, or steps in a different order than presented, or any combination of these. Further, the steps in other implementations of the invention may not be exactly the same as the steps presented and may be modified or altered as appropriate for a particular application or based on the data or situation.

For example, before step 2705, the doctor or a nurse may clean the surface of the target bone to be measured so that any fluids, such as blood, do not interfere with the measurements. However, there can be some fluids such as thin blood layer between the bone surface and the sensor because the layer will be very thin in comparison to with the bone thickness.

FIG. 28 shows one implementation of the invention where a bone oximeter probe is used during a surgical repair of a broken leg bone. The figure shows a side view of a patient's lower leg 2810 in which there is a fracture 2812 of a tibia bone 2815. A bone oximeter probe 2820 is inserted through an incision in soft tissue 2825. The probe is advanced through the soft tissue until a sensor head 2830 of the probe reaches or contacts a target bone (i.e., the tibia bone). Once the sensor head reaches or contacts a surface of the target bone, measurements of the bone can be made.

In a specific implementation, the system transmits optical signals into the target bone and receives reflected signals from the bone to determine, for example, a tissue oxygenation level, a hemoglobin concentration, or both. Other examples of bone measurements that may be made include information indicating blood vessel density of a region of the bone which is roughly proportional to the hemoglobin concentration.

These measurements can indicate to the doctor the health or viability of the bone and can help the surgeon determine or select a specific course of action. For example, in addition to screws and plates to repair the broken bone, additional reinforcement may also be used if oxygenation measurements of the bone indicate that the bone is unhealthy.

The system and methods for bone oximetry discussed in this application can be applied to any bone for which measurements are desired. Generally, any bone in the body (e.g., human or animal body) could be measured so long as the bone has a sufficient surface area for the sensor head and is accessible (e.g., accessible in surgery). For example, for spinal surgery, bone measurements can be made for the spine bone (e.g., lumbar vertebra). The sensor head can be placed on any part of the spine bone such as the spinous process, lamina, articular facet, transverse process (e.g., right and left transverse process), vertebral canal, or pedical. Bone measurements can be made for any type of bone, such as long bones, short bones, flat bones, irregular bones, sesamoid bones, cranial bones, the skull, the mandible, and facial bones. The bones may be located in the middle ear, throat, shoulder girdle, thorax, vertebral column, arms, hands, pelvis, thighs, legs, and feet.

Bones located in the shoulder girdle include the scapula or shoulder blade and the clavicle or collarbone. Bones located in the vertebral column include the cervical vertebrae, thoracic vertebrae, and lumbar vertebrae. Bones located in the arms and forearms include the humerus, radius, and ulna. Bones located in the hands include carpal or wrist bones (e.g., scaphoid, lunate, triquetral, pisiform, trapezium, trapezoid, capitate, and hamate bone), metacarpus or palm bones, and digits of the hands (e.g., proximal, intermediate, and distal phalanges). Bones located in the pelvis include the coccyx, sacrum, and hip bone. Bones located in the thighs and legs include the femur, patella, tibia, and fibula or fibular. Bones located in the feet include the tarsal or ankle bones (e.g., calcaneus, talus, navicular, medial cuneiform, intermediate cuneiform, lateral cuniform, and cuboid bone), and metatarsus bones.

To measure bone oxygenation, the sensor head may be placed on spongy bone (long bone horizontal section), medullary cavity marrow, muscle, adipose over periosteum, periostium, tendon, articular cartilage, meniscus, epiphysis, and periostium with little muscle or no muscle.

Furthermore, the bone oximeter probe and techniques for bone oximetry discussed in this application may be applied to nonhuman patients such as pigs (e.g., porcine bone measurements), dogs, cats, birds, horses, monkeys, rabbits, rats, apes, cows, and so forth. Specifically, the bone oximeter probe may be used to measure oxygen saturation of bovine long bone and the spinous process or skull of a pig.

A specific example of a surgical procedure in which the bone oximeter may be used includes an osteotomy such as an osteotomy of the hip, knee, or jaw. An osteotomy is a surgical operation where a bone is cut to shorten, lengthen, or change its alignment. It is sometimes performed to correct a hallux valgus, or to straighten a bone that has healed crookedly following a fracture. It is also used to correct a coxa vara, genu valgum, and genu varum. Osteotomy may be used to relieve pain in arthritis, especially of the hip and knee.

The bone oximeter probe may be used with tools for lateral lumbar surgery. Some of these tools are discussed in U.S. patent application Ser. Nos. 12/568,420, and 12/568,470 filed Sep. 28, 2009 which are incorporated by reference.

Another application for bone oximetry includes bone cancer or bone cancer treatments such as detecting bone cancer, treating bone cancer, and surgical procedures to remove bone cancer. Thus, in addition to using bone oximeter measurements in decision making as to whether or not to use specific bone graft additives such as bone morphogentic protein (BMP) to improve bone fusion outcomes, the sensor may also be used in assessing the viability of bone anywhere in the body. For example, in head and neck cancer surgery, tumors that occur in the jaw bone (oral cancers) may be radiated and then resected. However, all nonviable bone (often caused by radiation treatment damage, known as radioosteonecrosis) is typically removed along with the tumor. Information on what regions of the bone are nonviable can lead to reduced postoperative complications.

This application describes aspects of the invention in connection with a handheld bone oximeter tool or probe. However, the principles of the invention are also applicable to a bone oximeter tool or other tool with a bone oximeter sensor when implemented in an endoscopic instrument. Endoscopy is a minimally invasive diagnostic medical procedure that is used to assess the interior surfaces of an organ by inserting a tube into the body. At the end of the endoscope tool is a bone oximeter sensor or tool as described in this application.

The endoscopic instrument with a bone oximeter or other tool with a bone oximeter sensor at the end can have a robotic interface. The robotic interface allows a doctor control the instrument from a remote location. For example, the doctor in New York City can use a tool of the invention to perform a remote procedure on a patient who is located in Barrows, Ak. The doctor will be able to make oxygen saturation measurement of the patient's bone using the bone oximeter probe or other tool. The robotic interface may have a haptic interface which provides feedback to the doctor, or may not have a haptic interface. When a haptic interface for the tool is not available, the readings provided by the tool may give the doctor an indication of the condition of a bone.

A specific flow example for making a bone oximeter probe is presented below, but it should be understood that the invention is not limited to the specific flows and steps presented. A flow of the invention may have additional steps (not necessarily described in this application), different steps which replace some of the steps presented, fewer steps or a subset of the steps presented, or steps in a different order than presented, or any combination of these. Further, the steps in other implementations of the invention may not be exactly the same as the steps presented and may be modified or altered as appropriate for a particular application or situation.

In a specific implementation, a method includes:

1. Creating a set of channels, holes, or openings through a block. The channels are created such that they extend through the block, i.e., from a front surface of the block to a back surface of the block, opposite the front surface. Any technique may be used to create the channels. For example, the channels may be created by drilling, milling, boring, plunging, punching, laser cutting, or combinations of these.

2. Threading a fiber optic cable into each channel. That is, an end of the fiber optic cable is inserted into the channel. In a specific implementation, the end of the fiber optic cable is inserted through the back surface of the block and is advanced through the channel towards the front surface of the block. The fiber optic cable may be positioned within the channel such that the end is flush with the front surface, the end protrudes out from the front surface, or the end is recessed below the front surface. In another specific implementation, an opposite end of the fiber optic cable is inserted through front surface of the block, is advanced through the channel towards the back surface of the block, and exits the back surface.

3. Attaching the fiber optic cable to the channel. An adhesive such as epoxy may be used to attach the fiber optic cable to the channel. The epoxy may be applied at the back surface of the block, front surface of the block, or both and then allowed to flow into the channel.

4. Attaching the block to a distal end of a rigid elongated member. Epoxy may be used to attach the block to the elongated member. In a specific implementation, the fiber optic cable is threaded through the elongated member before the attaching the fiber optic cable to the channel in the block. That is, during the attaching the fiber optic cable to the channel, a portion of the fiber optic cable is lying in a passageway of the elongated member. In another implementation, the fiber optic cable is threaded through the elongated member after the attaching the fiber optic cable to the channel in the block.

In a specific implementation, a method for making a bone oximeter probe includes providing a sensor head cylinder and tube. Creating one or more holes in the sensor head cylinder. Attaching fiber optic cable to each of the one or more holes of the sensor head cylinder. Applying an adhesive such as epoxy to at least one of the sensor head cylinder or tube. Inserting the sensor head cylinder into the tube. In this specific implementation, a diameter of the sensor head cylinder is slightly less than an inner diameter of the tube. This simplifies manufacturing by allowing the sensor head cylinder to be inserted into the tube and providing a space for the adhesive to flow.

In a specific implementation, a method for making a bone oximeter probe having a pad to conform to a surface of a bone to be measured includes:

1. Attaching the pad to a block using, for example, an adhesive to join the pad and block together.

2. Creating a set of channels through the pad and block. The channels are created so that each channel extends from a front or bone facing or bone contacting surface of the pad to a back surface of the block, opposite the front surface. In a specific implementation, the channels are created after the pad and block are attached. In another implementation, the channels are created before the pad and block are attached. In this specific implementation, a first set of channels or holes are created in the pad. A second set of channels are created in the block. The first and second set of channels are then aligned and afterwards, the pad is attached to the block.

3. Threading a fiber optic cable into each channel.

4. Positioning the fiber optic cable within each channel so that an end of the fiber optic cable is flush with the front surface of the pad. In another implementation, the end of the optic cable is positioned so that it is below the front surface of the pad and between the front surface of the pad and the back surface of the block. That is, the end of the cable is recessed below the front surface of the pad so that there is a gap within the channel between the end of the cable and the front surface of the pad. In other words, a thickness of the block and pad in the uncompressed state (or a distance from the back surface of the block to the front surface of the pad) is greater than a distance from the back surface of the block to the end of the fiber optic cable. When the pad is compressed by being deformed around the surface of the bone, the end of the cable will be brought in close proximity to the surface of the bone.

5. Attaching the fiber optic cable to the channel.

6. Attaching the block to a distal end of a rigid elongated member (e.g., tube) such that at least a portion of the pad extends out from the distal end so that the pad can be compressed. In other words, a distance from a proximal end of the elongated member to the distal end is less than a distance from the proximal end to the front surface of the pad.

In a specific implementation, the attaching the block to the elongated member includes threading the fiber optic cable through a passageway in the elongated member after the attaching the fiber optic cable to the channel. In this specific implementation, the block and pad or end of the cable may be inserted into a proximal end of the elongated member and advanced towards the distal end. Alternatively, an opposite end of the cable may be inserted into the distal end of the elongated member and advanced towards the proximal end where it then exits the proximal end.

In another implementation, the attaching the block to the elongated member includes threading the fiber optic cable through a passageway in the elongated member before the attaching the fiber optic cable to the channel.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method for making a bone oximeter probe having a pad to conform to a surface of a bone to be measured, comprising:
   attaching the pad to a block;
   creating a plurality of channels through the pad and block, wherein each channel extends through the pad and block, from a front surface of the pad to a back surface of the block, opposite the front surface;
   threading a fiber optic cable into each channel of the plurality of channels;
   positioning the fiber optic cable within each channel so that an end of the fiber optic cable is flush with the front surface of the pad;
   attaching the fiber optic cable to the channel; and
   attaching the block to a distal end of a rigid tube, wherein at least a portion of the pad protrudes out from the distal end.

2. The method of claim 1 wherein a first portion of the pad comprising a first opening with a first fiber optic cable that can be subject to compression that is different from a second portion of the pad comprising a second opening with a second fiber optic cable.

3. The method of claim 2 wherein ends of the first and second fiber optic cables are exposed on the front surface of the pad, and an axis passing through the rigid tube passes through the front surface.

4. The method of claim 2 wherein ends of the first and second fiber optic cables are exposed on the front surface of the pad, and an axis passing through the rigid tube does not pass through the front surface.

5. The method of claim 2 wherein the pad and its first and second openings protrude in front of the distal end.

6. The method of claim 2 wherein the first and second openings are positioned on a sidewall of the rigid tube near the distal end of the elongated member.

7. The method of claim 1 comprising:
   providing a flexible tube, slidably extending from a proximal end of the rigid tube.

8. The method of claim 7 comprising:
   coupling a connector to the flexible tube.

9. The probe of claim 8 wherein the pad comprises a deformable material that can conform to a contour of the surface of the bone to be measured.

10. The probe of claim 8 wherein the sensor head comprises third and fourth openings, and in combination with light conducted via the first and second openings, light conducted via the third and fourth openings is used in making an oxygen saturation measurement for the bone.

11. The probe of claim 8 wherein to make an oxygen saturation measurement, the sensor head is adapted to be used on a surface of the bone to be measured.

12. The method of claim 1 wherein the pad comprises a surface being convex in one direction.

13. The method of claim 1 wherein the pad comprises a surface being convex in at least two directions.

14. The method of claim 1 wherein the pad comprises a surface being concave in one direction.

15. The method of claim 1 wherein the pad comprises a surface being concave in at least two directions.

* * * * *